US011077106B2

(12) United States Patent
Stuyckens et al.

(10) Patent No.: US 11,077,106 B2
(45) Date of Patent: Aug. 3, 2021

(54) CANCER TREATMENT

(71) Applicant: Janssen Pharmaceutica NV, Beerse (BE)

(72) Inventors: Kim Stuyckens, Heist-op-den-berg (BE); Juan Jose Perez Ruixo, Valencia (ES); Peter Marie Z. De Porre, Sint-Denijs-Westrem (BE); Anjali Narayan Avadhani, Chalfont, PA (US); Yohann Loriot, Villejuif (FR); Arlene O. Siefker-Radtke, Pearland, TX (US)

(73) Assignee: Janssen Pharmaceutica NV, Beerse (BE)

( * ) Notice: Subject to any disclaimer, the term of this patent is extended or adjusted under 35 U.S.C. 154(b) by 0 days.

(21) Appl. No.: 16/483,579

(22) PCT Filed: Feb. 2, 2018

(86) PCT No.: PCT/EP2018/052694
§ 371 (c)(1),
(2) Date: Aug. 5, 2019

(87) PCT Pub. No.: WO2018/141921
PCT Pub. Date: Aug. 9, 2018

(65) Prior Publication Data
US 2020/0022976 A1 Jan. 23, 2020

Related U.S. Application Data

(60) Provisional application No. 62/455,211, filed on Feb. 6, 2017.

(30) Foreign Application Priority Data

Dec. 20, 2017 (EP) .................................... 17209098

(51) Int. Cl.
*A61K 31/498* (2006.01)
*A61P 35/00* (2006.01)

(52) U.S. Cl.
CPC ............ *A61K 31/498* (2013.01); *A61P 35/00* (2018.01)

(58) Field of Classification Search
None
See application file for complete search history.

(56) References Cited

FOREIGN PATENT DOCUMENTS

WO    WO 2016/128411 A1    8/2016

OTHER PUBLICATIONS

The American Cancer Society medical and editorial content team, "What is Liver Cancer", American Cancer Society, downloaded on Jul. 31, 2020 from "https://www.cancer.org/cancer/liver-cancer/about/what-is-liver-cancer.html", revision date Apr. 1, 2019, 12 pages.*
MedicineNet, "Definition of Cancer", http://www.medicinenet.com/medterms-medical-dictionary/article.htm, 2015, 1 page.*
Tabernero, J., et al., "Phase I Dose-Escalation Study of JNJ-42756493, an Oral Pan-Fibroblast Growth Factor Receptor Inhibitor, in Patients With Advanced Solid Tumors", Journal of Clinical Oncology, (2015), vol. 33, No. 30, pp. 3401-3408.
Soria, J-C., et al., "Safety and activity of the pan-fibroblast growth factor receptor (FGFR) inhibitor erdafitinib in phase 1 study patients with advanced urothelial carcinoma", Annals of Oncology, (2016), 27 (Supplement 6), Abstracts.
Eisenhauer, E.A., et al., New response evaluation criteria in solid tumours: Revised RECIST guideline (version 1.1), European Journal of Cancer, (2009), vol. 45, No. 2, pp. 228-247.
National Cancer Institute, Common Terminology Criteria for Adverse Events (CTCAE), version 4.0, published May 28, 2009, (v4.03: Jun. 14, 2010), NCI, NIH, DHHS, NIH publication #09-7473, pp. 1-196.
International Search Report from PCT/EP2018/052694 dated Mar. 23, 2018.

* cited by examiner

*Primary Examiner* — Savitha M Rao
*Assistant Examiner* — Gregg Polansky
(74) *Attorney, Agent, or Firm* — BakerHostetler

(57) ABSTRACT

The present invention provides a method for the treatment of cancer with erdafitinib.

23 Claims, 2 Drawing Sheets

[a]Patients in the selected regimen were further uptitrated to 9 mg/d if they had not reached 5.5 mg/dL serum phosphate level by Day 14 and if they had no TRAEs.

CANCER TREATMENT

CROSS REFERENCE TO RELATED APPLICATIONS

This application is a national stage of PCT Application No. PCT/EP2018/052694, filed Feb. 2, 2018, which claims priority to U.S. Patent Application No. 62/455,211, filed Feb. 6, 2017 and to EPO Patent Application No. 17209098.7, filed Dec. 20, 2017, all of which are hereby incorporated by reference in their entirety.

The present invention provides for the treatment of cancer with erdafitinib with a high potential for response while limiting potential toxicities such as for example nail toxicities.

The present invention provides for treatment of cancer with erdafitinib that maximizes erdafitinib exposure while limiting potential toxicities.

The present invention provides for treatment of cancer with erdafitinib with a high objective response rate, in particular with an objective response rate of at least 40%, in particular with an objective response rate of at least 40% in chemo-naïve cancer patients, with an objective response rate of at least 40% in cancer patients who had disease progression after one prior line of chemotherapy, with an objective response rate of at least 40% in cancer patients who had disease progression after two or more prior lines of chemotherapy.

The present invention provides for treatment of cancer with erdafitinib with a short time to response, in particular with a median time to response less than 2 months.

DETAILED DESCRIPTION OF THE INVENTION

Figure 1:
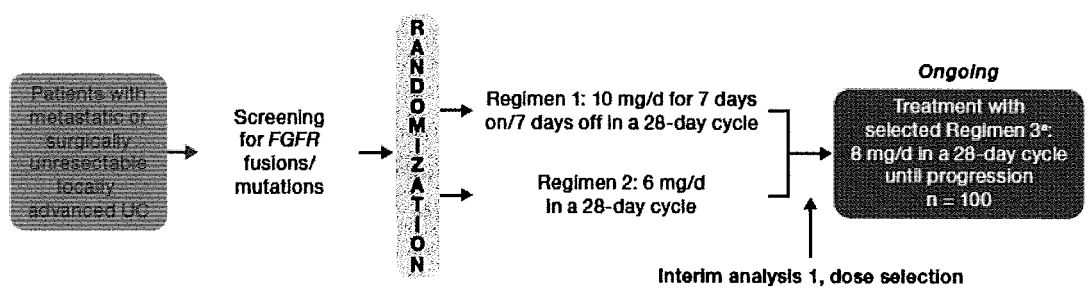
FIG. 1 represents the study scheme for the Phase 2, multicenter, open-label study to evaluate the efficacy and safety of erdafitinib in subjects with metastatic or surgically unresectable urothelial cancer harboring selected FGFR (fibroblast growth factor receptor) genetic alterations (FGFR translocations or mutations).

The present invention provides for the treatment of cancer with erdafitinib that maximizes erdafitinib exposure already within the first cycle of treatment (set at, for example, the first 28 days of treatment or the first 21 days of treatment, in particular with daily continuous dosing) as well as during further treatment cycles (set at, for example, 28 days/cycle or 21 days/cycle, in particular with daily continuous dosing) while limiting potential toxicities.

The present invention provides for treatment of cancer with erdafitinib that maximizes erdafitinib exposure and brings the subject in need of erdafitinib quickly at the target serum phosphate range, in particular ranging from and including 5.5 mg/dL to <7 mg/dL or ranging from and including 5.5 mg/dL to ≤9 mg/dL, to keep phosphate based toxicities under control.

Erdafitinib or N-(3,5-dimethoxyphenyl)-N'-(1-methylethyl)-N-[3-(1-methyl-1H-pyrazol-4-y)quinoxalin-6-yl]ethane-1,2-diamine is a pan-fibroblast growth factor receptor (FGFR 1,2,3,4) tyrosine kinase inhibitor.

The chemical structure of erdafitinib is

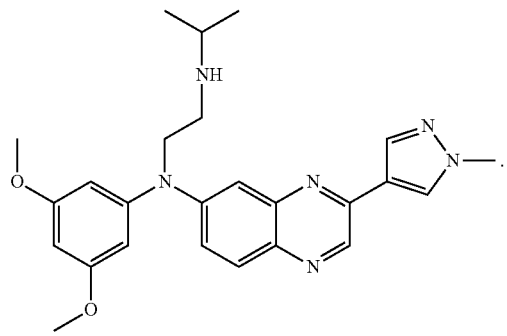

Serum phosphate levels may represent an on-target pharmacodynamic marker pointing towards FGFR target engagement by erdafitinib. Levels of serum phosphate are likely to increase with target engagement. But the serum phosphate levels need to be monitored to minimize or avoid or control acute and prolonged hyperphosphatemia.

It has been found that a higher proportion of patients are responding to erdafitinib treatment when serum phosphate levels are ≥5.5 mg/dL.

In an embodiment, the proportion of patients showing objective response rate is, depending on the cancer type, at least 15%, or 20%, or 25%, or 30%, or 35%, or 40%, or 45%, 50%, 55%, 60%, 65% or above 65%.

In an embodiment, the exposure to erdafitinib is such that it provides for an objective response rate, depending on the cancer type, of at least 15%, or 20%, or 25%, or 30%, or 35%, or 40%, or 45%, 50%, 55%, 60%, 65% or above 65%.

In an embodiment, the serum phosphate levels of the cancer patient is ≥5.5 mg/dL, in particular ranging from and including 5.5 mg/dL to <7 mg/dL or ranging from and including 5.5 mg/dL to ≤9 mg/dL, upon exposure to erdafitinib providing for an objective response rate, depending on the cancer type, of at least 15%, or 20%, or 25%, or 30%, or 35%, or 40%, or 45%, 50%, 55%, 60%, 65% or above 65%.

In an embodiment, the methods of treatment of cancer as described herein or the uses for the manufacture of a medicament for the treatment of cancer as described herein or erdafitinib for use in the treatment of cancer as described herein provide for an objective response rate of at least 15%, or 20%, or 25%, or 30%, or 35%, or 40%, or 45%, 50%, 55%, 60%, 65% or above 65%.

In an embodiment, the methods of treatment of cancer as described herein or the uses for the manufacture of a medicament for the treatment of cancer as described herein or erdafitinib for use in the treatment of cancer as described herein, wherein the cancer is urothelial cancer, metastatic or surgically unresectable urothelial cancer, in particular urothelial cancer, metastatic or surgically unresectable urothelial cancer with selected FGFR genetic alterations, provide for an objective response rate of at least 40%, in particular is about 40%, is about 41%, is about 42%, is about 43%, is about 44%, is about 45%, is about 46%, is about 47%, is about 48%, is about 49%, is about 50%. In particular, the objective response rate ranges from 40% to 50%, or ranges from 40% to 45%, or ranges from 42% to 45%, In an embodiment, for patients with urothelial cancer, metastatic or surgically unresectable urothelial cancer, in particular urothelial cancer, metastatic or surgically unresectable urothelial cancer with selected FGFR genetic alterations, the objective response rate upon exposure to erdafitinib according to the dosing regimens as disclosed herein, is at least 40%, in particular is about 40%, is about 41%, is about 42%, is about 43%, is about 44%, is about 45%, is about 46%, is about 47%, is about 48%, is about 49%, is about 50%. In particular, the objective response rate ranges from 40% to 50%, or ranges from 40% to 45%, or ranges from 42% to 45%, In an embodiment, the methods of treatment of cancer as described herein or the uses for the manufacture of a medicament for the treatment of cancer as described herein or erdafitinib for use in the treatment of cancer as described herein provide for a median duration of response of at least 4 months, or at least 5 months, or at least 6 months, or at least 7 months.

In an embodiment, the methods of treatment of cancer as described herein or the uses for the manufacture of a medicament for the treatment of cancer as described herein or erdafitinib for use in the treatment of cancer as described herein, wherein the cancer is urothelial cancer, metastatic or surgically unresectable urothelial cancer, in particular urothelial cancer, metastatic or surgically unresectable urothelial cancer with selected FGFR genetic alterations, provide for a median duration of response of at least 4 months, or at least 5 months, or at least 6 months, or at least 7 months, or is about 4 months, or about 5 months or about 6 months or about 7 months. In particular, the median duration of response ranges between 4 months and 7 months.

In an embodiment, for patients with urothelial cancer, metastatic or surgically unresectable urothelial cancer, in particular urothelial cancer, metastatic or surgically unresectable urothelial cancer with selected FGFR genetic alterations, the median duration of response upon exposure to erdafitinib according to the dosing regimens as disclosed herein, is at least 4 months, or at least 5 months, or at least 6 months, or at least 7 months, or is about 4 months, or about 5 months or about 6 months or about 7 months. In particular, the median duration of response ranges between 4 months and 7 months.

In an embodiment, the methods of treatment of cancer as described herein or the uses for the manufacture of a medicament for the treatment of cancer as described herein or erdafitinib for use in the treatment of cancer as described herein provide for a median progression free survival of at least 4 months, or at least 5 months, or at least 6 months, or at least 7 months.

In an embodiment, the methods of treatment of cancer as described herein or the uses for the manufacture of a medicament for the treatment of cancer as described herein or erdafitinib for use in the treatment of cancer as described herein, wherein the cancer is urothelial cancer, metastatic or surgically unresectable urothelial cancer, in particular urothelial cancer, metastatic or surgically unresectable urothelial cancer with selected FGFR genetic alterations, provide for a median progression free survival of at least 4 months, or at least 5 months, or at least 6 months, or at least 7 months, or is about 4 months, or about 5 months or about 6 months or about 7 months. In particular, the median progression free survival ranges between 4 months and 7 months.

In an embodiment, for patients with urothelial cancer, metastatic or surgically unresectable urothelial cancer, in particular urothelial cancer, metastatic or surgically unresectable urothelial cancer with selected FGFR genetic alterations, the median progression free survival upon exposure to erdafitinib according to the dosing regimens as disclosed herein, is at least 4 months, or at least 5 months, or at least 6 months, or at least 7 months, or is about 4 months, or about 5 months or about 6 months or about 7 months. In particular, the median progression free survival ranges between 4 months and 7 months.

The median time to response to the methods of treatment of cancer as described herein or the uses for the manufacture of a medicament for the treatment of cancer as described herein or erdafitinib for use in the treatment of cancer as described herein is very short. In an embodiment, the median time to response is less than 2 months, in particular less than 1.5 months, in particular is around 1.4 months.

In an embodiment, the methods of treatment of cancer as described herein or the uses for the manufacture of a medicament for the treatment of cancer as described herein or erdafitinib for use in the treatment of cancer as described herein, wherein the cancer is urothelial cancer, metastatic or surgically unresectable urothelial cancer, in particular urothelial cancer, metastatic or surgically unresectable urothelial cancer with selected FGFR genetic alterations, provide for a median time to response of less than 2 months, in particular less than 1.5 months, in particular is around 1.4 months.

In an embodiment, for patients with urothelial cancer, metastatic or surgically unresectable urothelial cancer, in particular urothelial cancer, metastatic or surgically unresectable urothelial cancer with selected FGFR genetic alterations, the median time to response upon exposure to erdafitinib according to the dosing regimens as disclosed herein, is less than 2 months, in particular less than 1.5 months, in particular is around 1.4 months.

Unexpectedly, it was found that the response to the treatments of cancer as described herein, in particular the treatment of urothelial cancer, metastatic or surgically unresectable urothelial cancer, in particular urothelial cancer, metastatic or surgically unresectable urothelial cancer with selected FGFR genetic alterations, is independent of the number of prior lines treatment received by the patient, e.g. a chemo-naïve patient, in particular a chemo-naïve patient ineligible for cisplatin, a patient who had disease progression after one prior line of chemotherapy or a patient who had disease progression after two or more prior lines of chemotherapy. In an embodiment, the response to the treatment is similar for patients with different numbers of prior lines of treatment received, e.g. a chemo-naïve patient, in particular a chemo-naïve patient ineligible for cisplatin, a patient who had disease progression after one prior line of chemotherapy or a patient who had disease progression after two or more prior lines of chemotherapy. In an embodiment, the response to the treatments of cancer by patients with prior line chemotherapy, e.g. a patient who had disease progression after one prior line of chemotherapy or a patient who had disease progression after two or more prior lines of chemotherapy, is not worse than for chemo-naïve patients.

It has been found that serum phosphate levels of ≥7 mg/dL, in particular >9 mg/dL, may warrant temporary erdafitinib treatment interruption or erdafitinib dose adjustment (dose decrease).

In an embodiment temporary erdafitinib interruption represents interruption of erdafitinib administration until serum phosphate levels are again <5.5 mg/dL.

In an embodiment temporary erdafitinib interruption represents interruption of erdafitinib administration until serum phosphate levels are again <7 mg/dL.

It has been found that an efficacious and safe treatment with erdafitinib is administering erdafitinib in a therapeutically effective dose such that the serum phosphate levels range from and including 5.5 mg/dL to <7 mg/dL or range from and including 5.5 mg/dL to ≤9 mg/dL.

Serum phosphate levels can be measured with commercially available kits such as for example ab65622 Phosphate Assay Kit (Colorimetric) (Abcam).

It has been found that with a dose of 8 mg of erdafitinib daily, preferably once daily, on a continuous basis (every day, no treatment interruption, no intermittent administration unless the contexts indicates differently) the potential for the subject in need of erdafitinib administration, in particular the cancer patient, to reach or cross the 5.5 mg/dL serum phosphate levels increases, while minimizing the need for treatment interruption or dose reduction for potential drug related adverse events.

It has been found that with a dose of 8 mg of erdafitinib daily, preferably once daily, on a continuous basis the 5.5 mg/dL serum phosphate levels may be reached in the first cycle (set at, for example, the first 28 days or the first 21 days) of erdafitinib treatment. It has been found that with a dose of 8 mg of erdafitinib daily, preferably once daily, on a continuous basis the potential for the subject in need of erdafitinib administration, in particular the cancer patient, to reach or cross the 5.5 mg/dL serum phosphate levels early enough during the first cycle (e.g. at day 14±2 days of the treatment) of erdafitinib treatment increases to maximize efficacious treatment while minimizing the need for treatment interruption or dose reduction for potential drug related adverse events.

In an embodiment the serum phosphate levels of the subject in need of erdafitinib treatment, in particular the cancer patient, are monitored.

In an embodiment the serum phosphate levels of the subject in need of erdafitinib treatment, in particular the cancer patient, are monitored and early onset toxicity linked to FGFR inhibitors in general or to erdafitinib specifically shown by the subject, in need of erdafitinib treatment, in particular the cancer patient, are monitored.

In an embodiment early onset toxicity linked to FGFR inhibitors in general or to erdafitinib specifically comprise grade 3 or higher xerostomia or stomatitis/mucositis, dry skin, dry eye, nail toxicity (or grade 2 if lasting more than 1 week) or grade 2 or higher eye toxicity (keratitis, central serous retinopathy/retinal pigment epithelial detachments). Early onset toxicity may warrant treatment interruption or dose reduction. It is up to the discretion of the physician and it may depend on the disease state of the patient.

In an embodiment early onset toxicity or early onset toxicity linked to FGFR inhibitors in general or to erdafitinib specifically as described herein means clinically significant toxicity considered related to FGFR inhibitors in general or to erdafitinib specifically, usually considered to be grade 3 or higher, consisting of one or more of the following: stomatitis/mucositis, dry skin, dry eye, nail toxicity or specific eye toxicity (keratitis, or retinopathy also described as central serous retinopathy, retinal detachment, retinal edema, retinal pigment epithelial detachment, chorioretinopathy) or pertaining to other significant toxicity considered related to FGFR inhibitors in general or to erdafitinib specifically. Early onset toxicity may warrant treatment interruption or dose reduction. It is up to the discretion of the physician and it may depend on the disease state of the patient.

The present invention concerns a method for the treatment of cancer, which method comprises administering to a subject in need thereof, in particular a cancer patient, an amount of erdafitinib so that the levels of serum phosphate range from and including 5.5 mg/dL to <7 mg/dL. In an embodiment, the amount of erdafitinib is 8 mg, in particular 8 mg daily administered on a continuous basis. The present invention concerns a method for the treatment of cancer, which method comprises administering to a subject in need thereof, in particular a cancer patient, an amount of erdafitinib so that the levels of serum phosphate attain, within the first cycle of erdafitinib administration (a treatment cycle duration set at, for example, the first 28 days of administration or the first 21 days of administration and the serum phosphate level assessed at or around the $28^{th}$ day, or at or around the $21^{st}$ day or at or around the $14^{th}$ day of administration) the range from and including 5.5 mg/dL to <7 mg/dL. In an embodiment, the amount of erdafitinib is 8 mg, in particular 8 mg daily administered on a continuous basis.

The present invention concerns a method for the treatment of cancer, which method comprises administering to a subject in need thereof, in particular a cancer patient, an amount of erdafitinib so that the levels of serum phosphate range from and including 5.5 mg/dL to ≤9 mg/dL. In an embodiment, the amount of erdafitinib is 8 mg, in particular 8 mg daily administered on a continuous basis. The present invention concerns a method for the treatment of cancer, which method comprises administering to a subject in need thereof, in particular a cancer patient, an amount of erdafitinib so that the levels of serum phosphate attain, within the first cycle of erdafitinib administration (a treatment cycle duration set at, for example, the first 28 days of administration or the first 21 days of administration and the serum phosphate level assessed at or around the $28^{th}$ day, or at or around the $21^{st}$ day or at or around the $14^{th}$ day of administration) the range from and including 5.5 mg/dL to ≤9 mg/dL. In an embodiment, the amount of erdafitinib is 8 mg, in particular 8 mg daily administered on a continuous basis.

The present invention concerns the use of erdafitinib for the manufacture of a medicament for the treatment of cancer, in an amount so that the levels of serum phosphate range from and including 5.5 mg/dL to <7 mg/dL. The present invention concerns the use of erdafitinib for the manufacture of a medicament for the treatment of cancer, in an amount so that the levels of serum phosphate attain, within the first cycle of erdafitinib administration (a treatment cycle duration set at, for example, the first 28 days of administration or the first 21 days of administration and the serum phosphate level assessed at or around the $28^{th}$ day, or at or around the $21^{st}$ day or at or around the $14^{th}$ day of administration) the range from and including 5.5 mg/dL to <7 mg/dL. In an embodiment, the amount of erdafitinib is 8 mg, in particular 8 mg daily administered on a continuous basis.

The present invention concerns the use of erdafitinib for the manufacture of a medicament for the treatment of cancer, in an amount so that the levels of serum phosphate range from and including 5.5 mg/dL to ≤9 mg/dL. The present invention concerns the use of erdafitinib for the manufacture of a medicament for the treatment of cancer, in an amount so that the levels of serum phosphate attain, within the first cycle of erdafitinib administration (a treatment cycle duration set at, for example, the first 28 days of administration or the first 21 days of administration and the serum phosphate level assessed at or around the $28^{th}$ day, or at or around the $21^{st}$ day or at or around the $14^{th}$ day of administration) the range from and including 5.5 mg/dL to ≤9 mg/dL. In an embodiment, the amount of erdafitinib is 8 mg, in particular 8 mg daily administered on a continuous basis.

The present invention concerns erdafitinib for use in the treatment of cancer, wherein erdafitinib is administered in an amount so that the levels of serum phosphate range from and including 5.5 mg/dL to <7 mg/dL. The present invention concerns erdafitinib for use in the treatment of cancer, wherein erdafitinib is administered in an amount so that the levels of serum phosphate attain, within the first cycle of erdafitinib administration (a treatment cycle duration set at, for example, the first 28 days of administration or the first 21 days of administration and the serum phosphate level assessed at or around the $28^{th}$ day, or at or around the $21^{st}$ day or at or around the $14^{th}$ day of administration) the range from and including 5.5 mg/dL to <7 mg/dL. In an embodiment, the amount of erdafitinib is 8 mg, in particular 8 mg daily administered on a continuous basis.

The present invention concerns erdafitinib for use in the treatment of cancer, wherein erdafitinib is administered in an amount so that the levels of serum phosphate range from and including 5.5 mg/dL to ≤9 mg/dL. The present invention concerns erdafitinib for use in the treatment of cancer, wherein erdafitinib is administered in an amount so that the levels of serum phosphate attain, within the first cycle of erdafitinib administration (a treatment cycle duration set at, for example, the first 28 days of administration or the first 21 days of administration and the serum phosphate level assessed at or around the $28^{th}$ day, or at or around the $21^{st}$ day or at or around the $14^{th}$ day of administration) the range from and including 5.5 mg/dL to ≤9 mg/dL. In an embodiment, the amount of erdafitinib is 8 mg, in particular 8 mg daily administered on a continuous basis.

The present invention concerns a method for the treatment of cancer, which method comprises administering to a subject in need thereof, in particular a cancer patient, 8 mg of erdafitinib daily, in particular once daily, on a continuous basis. Dose adjustment may be done based on serum phosphate level and observed or absence of toxicity.

The present invention concerns the use of erdafitinib for the manufacture of a medicament for the treatment of cancer, wherein the medicament comprises erdafitinib in an amount of 8 mg and wherein the medicament is for daily, in particular once daily, administration on a continuous basis. Dose adjustment may be done based on serum phosphate level and observed or absence of toxicity.

The present invention concerns erdafitinib for use in the treatment of cancer, wherein erdafitinib is administered in an amount of 8 mg daily, in particular once daily, on a continuous basis. Dose adjustment may be done based on serum phosphate level and observed or absence of toxicity.

During the treatment of erdafitinib at a dose of 8 mg daily, preferably once daily, on a continuous basis, serum phosphate levels can be monitored. If the levels of serum phosphate are <5.5 mg/dL, then the dose of erdafitinib can be increased, can be up-titrated to 9 mg daily, preferably once daily, on a continuous basis. In an embodiment, the levels of serum phosphate for determining whether or not to up-titrate are measured on a treatment day during the first cycle of erdafitinib treatment, in particular on day 14±2 days, more in particular on day 14, of erdafitinib administration.

During the treatment of erdafitinib at a dose of 8 mg daily, preferably once daily, on a continuous basis, serum phosphate levels can be monitored. If the levels of serum phosphate are <7 mg/dL or range from and include 7 mg/dL to ≤9 mg/dL or are ≤9 mg/dL, then the dose of erdafitinib can be increased, can be up-titrated to 9 mg daily, preferably once daily, on a continuous basis. In an embodiment, the levels of serum phosphate for determining whether or not to up-titrate are measured on a treatment day during the first cycle of erdafitinib treatment, in particular on day 14±2 days, more in particular on day 14, of erdafitinib administration.

The present invention concerns a method for the treatment of cancer, which method comprises administering to a subject in need thereof, in particular a cancer patient, 8 mg of erdafitinib daily, in particular once daily, on a continuous basis which method comprises monitoring of serum phosphate levels of the subject. In an embodiment, the levels of serum phosphate for determining whether or not to up-titrate are measured on a treatment day during the first cycle of erdafitinib treatment, in particular on day 14±2 days, more in particular on day 14, of erdafitinib administration.

The present invention concerns the use of erdafitinib for the manufacture of a medicament for the treatment of cancer in a cancer patient, wherein the medicament comprises erdafitinib in an amount of 8 mg, wherein the medicament is for daily, in particular once daily, administration on a continuous basis and wherein serum phosphate levels of the cancer patient are monitored. In an embodiment, the levels of serum phosphate for determining whether or not to up-titrate are measured on a treatment day during the first cycle of erdafitinib treatment, in particular on day 14±2 days, more in particular on day 14, of erdafitinib administration.

The present invention concerns erdafitinib for use in the treatment of cancer in a cancer patient, wherein erdafitinib is administered in an amount of 8 mg daily, in particular once daily, on a continuous basis and wherein the serum phosphate levels of the cancer patient are monitored. In an embodiment, the levels of serum phosphate for determining whether or not to up-titrate are measured on a treatment day during the first cycle of erdafitinib treatment, in particular on day 14±2 days, more in particular on day 14, of erdafitinib administration.

The present invention concerns a method for the treatment of cancer, which method comprises administering to a subject in need thereof, in particular a cancer patient, 8 mg of erdafitinib daily, in particular once daily, on a continuous basis, which method comprises monitoring of serum phosphate levels of the subject and when the serum phosphate levels are <5.5 mg/dL, the daily amount, preferably the once daily amount, of erdafitinib administered on a continuous basis, is increased to 9 mg. When the serum phosphate levels range from and including 5.5 mg/dL to <7 mg/dL, the subject remains on the 8 mg daily continuous treatment. When the serum phosphate levels are ≥7 mg/dL, the treatment is interrupted temporarily, in particular erdafitinib treatment is interrupted until serum phosphate levels are again <7 mg/dL, or the daily continuous dose is adjusted to <8 mg, in particular the treatment is interrupted temporarily, in particular until serum phosphate levels are <5.5 mg/dL. In an embodiment, the levels of serum phosphate are measured on a treatment day during the first cycle of erdafitinib treatment, in particular on day 14±2 days, more in particular on day 14, of erdafitinib administration. In an embodiment, when the serum phosphate levels are ≥7 mg/dL, in particular range from and including 7 mg/dL to ≤9 mg/dL, in particular on day 14±2 days, more in particular on day 14, the treatment is interrupted temporarily until serum phosphate levels are <5.5 mg/dL and then erdafitinib treatment is re-started with 8 mg daily, in particular once daily, on a continuous basis.

In an embodiment, serum phosphate levels during further erdafitinib administration may be managed according to Table 3.

The present invention concerns a method for the treatment of cancer, which method comprises administering to a subject in need thereof, in particular a cancer patient, 8 mg of erdafitinib daily, in particular once daily, on a continuous basis, which method comprises monitoring of serum phosphate levels of the subject and when the serum phosphate levels are <7 mg/dL, the daily amount, preferably the once daily amount, of erdafitinib administered on a continuous basis, is increased to 9 mg. When the serum phosphate levels range from and including 7 mg/dL to ≤9 mg/dL, the daily amount, preferably the once daily amount, of erdafitinib administered on a continuous basis, is increased to 9 mg, while concurrently treatment with a phosphate binder, such as for example sevelamer, is optionally initiated. In an embodiment, concurrent treatment with a phosphate binder, such as for example sevelamer, is initiated. When the serum phosphate levels are elevated to >9 mg/dL, the treatment is interrupted temporarily, in particular erdafitinib treatment is interrupted until serum phosphate levels are again <7 mg/dL, and, upon serum phosphate being below 7 mg/dL, the daily continuous dose is adjusted to the same or a lower daily dose. In case of persistent serum phosphate levels ≥10 mg/dL for ≥2 weeks, the treatment is interrupted permanently, in particular erdafitinib treatment is interrupted permanently. In an embodiment, the levels of serum phosphate are measured on a treatment day during the first cycle of erdafitinib treatment, in particular on day 14±2 days, more in particular on day 14, of erdafitinib administration. In an embodiment, when the serum phosphate levels are >9 mg/dL, the treatment is interrupted temporarily until serum phosphate levels are <7 mg/dL and then erdafitinib treatment is re-started with 8 mg daily, in particular once daily, on a continuous basis. In an embodiment, serum phosphate levels during further erdafitinib administration may be managed according to Table 4.

The present invention concerns a method for the treatment of cancer, which method comprises administering to a subject in need thereof, in particular a cancer patient, 8 mg of erdafitinib daily, in particular once daily, on a continuous basis, which method comprises monitoring of serum phosphate levels of the subject and monitoring of early onset toxicity linked to FGFR inhibitors in general or to erdafitinib specifically shown by the subject, and when the serum phosphate levels are <5.5 mg/dL and no early onset toxicity is shown, the daily amount, preferably the once daily amount, of erdafitinib administered on a continuous basis, is increased to 9 mg. When the serum phosphate levels range from and including 5.5 mg/dL to <7 mg/dL and no early onset toxicity is shown, the subject remains on the 8 mg daily continuous treatment. When the serum phosphate levels are ≥7 mg/dL, the treatment is interrupted temporarily, in particular erdafitinib treatment is interrupted until serum phosphate levels are again <7 mg/dL, or the daily continuous dose is adjusted to <8 mg, in particular the treatment is interrupted temporarily, in particular until serum phosphate levels are <5.5 mg/dL. In an embodiment, the levels of serum phosphate are measured on a treatment day during the first cycle of erdafitinib treatment, in particular on day 14±2 days, more in particular on day 14, of erdafitinib administration. In an embodiment, when the serum phosphate levels are ≥7 mg/dL, the treatment is interrupted temporarily until serum phosphate levels are <5.5 mg/dL and then erdafitinib treatment is re-started with 8 mg daily, in particular once daily, on a continuous basis. In an embodiment, serum phosphate levels during further erdafitinib administration may be managed according to Table 3.

The present invention concerns a method for the treatment of cancer, which method comprises administering to a subject in need thereof, in particular a cancer patient, 8 mg of erdafitinib daily, in particular once daily, on a continuous basis, which method comprises monitoring of serum phosphate levels of the subject and monitoring of early onset toxicity linked to FGFR inhibitors in general or to erdafitinib specifically shown by the subject, and when the serum phosphate levels are <7 mg/dL and no early onset toxicity is shown, the daily amount, preferably the once daily amount, of erdafitinib administered on a continuous basis, is increased to 9 mg. When the serum phosphate levels range from and including 7 mg/dL to ≤9 mg/dL and no early onset toxicity is shown, the daily amount, preferably the once daily amount, of erdafitinib administered on a continuous basis, is increased to 9 mg, while concurrently treatment with a phosphate binder, such as for example sevelamer, is optionally initiated. In an embodiment, concurrent treatment with a phosphate binder, such as for example sevelamer, is initiated. When the serum phosphate levels are elevated >9 mg/dL, the treatment is interrupted temporarily, in particular erdafitinib treatment is interrupted until serum phosphate levels are again <7 mg/dL, and, upon serum phosphate being below 7 mg/dL, the daily continuous dose is adjusted to the same or a lower daily dose. In an embodiment, the levels of serum phosphate are measured on a treatment day during the first cycle of erdafitinib treatment, in particular on day 14±2 days, more in particular on day 14, of erdafitinib administration. In an embodiment, when the serum phosphate levels are >9 mg/dL, the treatment is interrupted temporarily until serum phosphate levels are <7 mg/dL and then erdafitinib treatment is re-started with 8 mg daily, in particular once daily, on a continuous basis.

In an embodiment, serum phosphate levels during further erdafitinib administration may be managed according to Table 4.

The present invention concerns a method for the treatment of cancer, which method comprises administering to a subject in need thereof, in particular a cancer patient, 9 mg of erdafitinib daily, in particular once daily, on a continuous basis, which method comprises monitoring of serum phosphate levels of the subject and wherein the 9 mg is administered to the subject when the serum phosphate levels of said subject are <5.5 mg/dL while being on a treatment with erdafitinib 8 mg daily, in particular once daily, on a continuous basis. In an embodiment, the levels of serum phosphate are measured on a treatment day during the first cycle of erdafitinib treatment, in particular on day 14±2 days, more in particular on day 14, of erdafitinib administration.

In an embodiment, serum phosphate levels during further erdafitinib administration may be managed according to Table 3.

The present invention concerns a method for the treatment of cancer, which method comprises administering to a subject in need thereof, in particular a cancer patient, 9 mg of erdafitinib daily, in particular once daily, on a continuous basis, wherein the 9 mg is administered to the subject when the serum phosphate levels of said subject are <7 mg/dL or when the serum phosphate levels range from and including 7 mg/dL to ≤9 mg/dL, while being on a treatment with erdafitinib 8 mg daily, in particular once daily, on a continuous basis. When the serum phosphate levels range from and including 7 mg/dL to ≤9 mg/dL, concurrent treatment with a phosphate binder, such as for example sevelamer, may be initiated. In an embodiment, concurrent treatment with a phosphate binder, such as for example sevelamer, is initiated. In an embodiment, the levels of serum phosphate are measured on day 14±2 days, in particular on day 14, of erdafitinib administration. In an embodiment, serum phosphate levels during further erdafitinib administration may be managed according to Table 4.

The present invention concerns a method for the treatment of cancer, which method comprises administering to a subject in need thereof, in particular a cancer patient, 9 mg of erdafitinib daily, in particular once daily, on a continuous basis, wherein the 9 mg is administered to the subject when the serum phosphate levels of said subject are <5.5 mg/dL and no early onset toxicity is shown while being on a treatment with erdafitinib 8 mg daily, in particular once daily, on a continuous basis. In an embodiment, the levels of serum phosphate are measured on a treatment day during the first cycle of erdafitinib treatment, in particular on day 14±2 days, more in particular on day 14, of erdafitinib administration.

In an embodiment, serum phosphate levels during further erdafitinib administration may be managed according to Table 3.

The present invention concerns a method for the treatment of cancer, which method comprises administering to a subject in need thereof, in particular a cancer patient, 9 mg of erdafitinib daily, in particular once daily, on a continuous basis, wherein the 9 mg is administered to the cancer patient when the serum phosphate levels of said patient are <7 mg/dL or when the serum phosphate levels range from and including 7 mg/dL to ≤9 mg/dL, and no early onset toxicity is shown while being on a treatment with erdafitinib 8 mg daily, in particular once daily, on a continuous basis. When the serum phosphate levels range from and including 7 mg/dL to ≤9 mg/dL and no early onset toxicity is shown, concurrent treatment with a phosphate binder, such as for example sevelamer, may be initiated. In an embodiment, concurrent treatment with a phosphate binder, such as for example sevelamer, is initiated. In an embodiment, the levels of serum phosphate are measured on a treatment day during the first cycle of erdafitinib treatment, in particular on day 14±2 days, more in particular on day 14, of erdafitinib administration.

In an embodiment, serum phosphate levels during further erdafitinib administration may be managed according to Table 4.

The present invention concerns the use of erdafitinib for the manufacture of a medicament for the treatment of cancer in a cancer patient, wherein the medicament comprises erdafitinib in an amount of 8 mg and wherein the medicament is for daily, in particular once daily, administration on a continuous basis, wherein serum phosphate levels of the cancer patient are monitored and when the serum phosphate levels are <5.5 mg/dL, the amount of erdafitinib in the medicament for daily, in particular once daily, administration on a continuous basis is increased to 9 mg. When the serum phosphate levels range from and including 5.5 mg/dL to <7 mg/dL, the patient remains on the 8 mg daily continuous treatment. When the serum phosphate levels are >7 mg/dL, the treatment is interrupted temporarily, in particular erdafitinib treatment is interrupted until serum phosphate levels are again <7 mg/dL, or the daily continuous dose is adjusted to <8 mg, in particular the treatment is interrupted temporarily, in particular until serum phosphate levels are <5.5 mg/dL. In an embodiment, the levels of serum phosphate are measured on a treatment day during the first cycle of erdafitinib treatment, in particular on day 14±2 days, more in particular on day 14, of erdafitinib administration. In an embodiment, when the serum phosphate levels are ≥7 mg/dL, the treatment is interrupted temporarily until serum phosphate levels are <5.5 mg/dL and then erdafitinib treatment is re-started with 8 mg daily, in particular once daily, on a continuous basis.

In an embodiment, serum phosphate levels during further erdafitinib administration may be managed according to Table 3.

The present invention concerns the use of erdafitinib for the manufacture of a medicament for the treatment of cancer in a cancer patient, wherein the medicament comprises erdafitinib in an amount of 8 mg and wherein the medicament is for daily, in particular once daily, administration on a continuous basis, wherein serum phosphate levels of the cancer patient are monitored and when the serum phosphate levels are <7 mg/dL, the amount of erdafitinib in the medicament for daily, in particular once daily, administration on a continuous basis, is increased to 9 mg. When the serum phosphate levels range from and including 7 mg/dL to ≤9 mg/dL, the amount of erdafitinib for daily, in particular once daily, administration on a continuous basis, is increased to 9 mg, while concurrently treatment with a phosphate binder, such as for example sevelamer, is optionally initiated. In an embodiment, concurrent treatment with a phosphate binder, such as for example sevelamer, is initiated. When the serum phosphate levels are elevated >9 mg/dL, the treatment is interrupted temporarily, in particular erdafitinib treatment is interrupted until serum phosphate levels are again <7 mg/dL, and, upon serum phosphate being below 7 mg/dL, the daily continuous dose is adjusted to the same or a lower daily dose. In an embodiment, the levels of serum phosphate are measured on a treatment day during the first cycle of erdafitinib treatment, in particular on day 14±2 days, more in particular on day 14, of erdafitinib administration. In an embodiment, when the serum phosphate levels are >9 mg/dL, the treatment is interrupted temporarily until serum phosphate levels are <7 mg/dL and then erdafitinib treatment is re-started with 8 mg daily, in particular once daily, on a continuous basis.

In an embodiment, serum phosphate levels during further erdafitinib administration may be managed according to Table 4.

The present invention concerns the use of erdafitinib for the manufacture of a medicament for the treatment of cancer in a cancer patient, wherein the medicament comprises erdafitinib in an amount of 8 mg and wherein the medicament is for daily, in particular once daily, administration on a continuous basis, wherein serum phosphate levels of the cancer patient are monitored and early onset toxicity linked to FGFR inhibitors in general or to erdafitinib specifically shown by the cancer patient is monitored, and when the serum phosphate levels are <5.5 mg/dL and no early onset toxicity is shown, the amount of erdafitinib in the medicament for daily, in particular once daily, administration on a continuous basis is increased to 9 mg. When the serum phosphate levels range from and including 5.5 mg/dL to <7 mg/dL and no early onset toxicity is shown, the patient remains on the 8 mg daily continuous treatment. When the serum phosphate levels are ≥7 mg/dL, the treatment is interrupted temporarily, in particular erdafitinib treatment is interrupted until serum phosphate levels are again <7 mg/dL, or the daily continuous dose is adjusted to <8 mg, in particular the treatment is interrupted temporarily, in particular until serum phosphate levels are <5.5 mg/dL. In an embodiment, the levels of serum phosphate are measured on a treatment day during the first cycle of erdafitinib treatment, in particular on day 14±2 days, more in particular on day 14, of erdafitinib administration. In an embodiment, when the serum phosphate levels are ≥7 mg/dL, the treatment is interrupted temporarily until serum phosphate levels are <5.5 mg/dL and then erdafitinib treatment is re-started with 8 mg daily, in particular once daily, on a continuous basis.

In an embodiment, serum phosphate levels during further erdafitinib administration may be managed according to Table 3.

The present invention concerns the use of erdafitinib for the manufacture of a medicament for the treatment of cancer in a cancer patient, wherein the medicament comprises erdafitinib in an amount of 8 mg and wherein the medicament is for daily, in particular once daily, administration on a continuous basis, wherein serum phosphate levels of the cancer patient are monitored and early onset toxicity linked to FGFR inhibitors in general or to erdafitinib specifically shown by the cancer patient is monitored, and when the serum phosphate levels are <7 mg/dL and no early onset toxicity is shown, the amount of erdafitinib in the medicament for daily, in particular once daily, administration on a continuous basis, is increased to 9 mg. When the serum phosphate levels range from and including 7 mg/dL to ≤9 mg/dL and no early onset toxicity is shown, the amount of erdafitinib for daily, in particular once daily, administration on a continuous basis, is increased to 9 mg, while concurrently treatment with a phosphate binder, such as for example sevelamer, is optionally initiated. In an embodiment, concurrent treatment with a phosphate binder, such as for example sevelamer, is initiated. When the serum phosphate levels are elevated >9 mg/dL, the treatment is interrupted temporarily, in particular erdafitinib treatment is interrupted until serum phosphate levels are again <7 mg/dL, and, upon serum phosphate being below 7 mg/dL, the daily continuous dose is adjusted to the same or a lower daily dose. In an embodiment, the levels of serum phosphate are measured on a treatment day during the first cycle of erdafitinib treatment, in particular on day 14±2 days, more in particular on day 14, of erdafitinib administration. In an embodiment, when the serum phosphate levels are >9 mg/dL, the treatment is interrupted temporarily until serum phosphate levels are <7 mg/dL and then erdafitinib treatment is re-started with 8 mg daily, in particular once daily, on a continuous basis. In an embodiment, serum phosphate levels during further erdafitinib administration may be managed according to Table 4.

The present invention concerns the use of erdafitinib for the manufacture of a medicament for the treatment of cancer in a cancer patient, wherein the medicament comprises erdafitinib in an amount of 9 mg and wherein the medicament is for daily, in particular once daily, administration on a continuous basis, wherein the medicament is administered to the cancer patient when the serum phosphate levels of said patient are <5.5 mg/dL while being on a treatment with erdafitinib 8 mg daily, in particular once daily, on a continuous basis. In an embodiment, the levels of serum phosphate are measured on a treatment day during the first cycle of erdafitinib treatment, in particular on day 14±2 days, more in particular on day 14, of erdafitinib administration.

In an embodiment, serum phosphate levels during further erdafitinib administration may be managed according to Table 3.

The present invention concerns the use of erdafitinib for the manufacture of a medicament for the treatment of cancer in a cancer patient, wherein the medicament comprises erdafitinib in an amount of 9 mg and wherein the medicament is for daily, in particular once daily, administration on a continuous basis, wherein the medicament is administered to the cancer patient when the serum phosphate levels of said patient are <7 mg/dL or when the serum phosphate levels range from and including 7 mg/dL to ≤9 mg/dL, while being on a treatment with erdafitinib 8 mg daily, in particular once daily, on a continuous basis. When the serum phosphate levels range from and including 7 mg/dL to ≤9 mg/dL, concurrent treatment with a phosphate binder, such as for example sevelamer, may be initiated. In an embodiment, concurrent treatment with a phosphate binder, such as for example sevelamer, is initiated. In an embodiment, the levels of serum phosphate are measured on a treatment day during the first cycle of erdafitinib treatment, in particular on day 14±2 days, more in particular on day 14, of erdafitinib administration.

In an embodiment, serum phosphate levels during further erdafitinib administration may be managed according to Table 4.

The present invention concerns the use of erdafitinib for the manufacture of a medicament for the treatment of cancer in a cancer patient, wherein the medicament comprises erdafitinib in an amount of 9 mg and wherein the medicament is for daily, in particular once daily, administration on a continuous basis, wherein the medicament is administered to the cancer patient when the serum phosphate levels of said patient are <5.5 mg/dL and no early onset toxicity is shown while being on a treatment with erdafitinib 8 mg daily, in particular once daily, on a continuous basis. In an embodiment, the levels of serum phosphate are measured on a treatment day during the first cycle of erdafitinib treatment, in particular on day 14±2 days, more in particular on day 14, of erdafitinib administration. In an embodiment, serum phosphate levels during further erdafitinib administration may be managed according to Table 3.

The present invention concerns the use of erdafitinib for the manufacture of a medicament for the treatment of cancer in a cancer patient, wherein the medicament comprises erdafitinib in an amount of 9 mg and wherein the medicament is for daily, in particular once daily, administration on a continuous basis, wherein the medicament is administered to the cancer patient when the serum phosphate levels of said patient are <7 mg/dL or when the serum phosphate levels range from and including 7 mg/dL to ≤9 mg/dL, and no early onset toxicity is shown while being on a treatment with erdafitinib 8 mg daily, in particular once daily, on a continuous basis. When the serum phosphate levels range from and including 7 mg/dL to ≤9 mg/dL and no early onset toxicity is shown, concurrent treatment with a phosphate binder, such as for example sevelamer, may be initiated. In an embodiment, concurrent treatment with a phosphate binder, such as for example sevelamer, is initiated. In an embodiment, the levels of serum phosphate are measured on a treatment day during the first cycle of erdafitinib treatment, in particular on day 14±2 days, more in particular on day 14, of erdafitinib administration.

In an embodiment, serum phosphate levels during further erdafitinib administration may be managed according to Table 4.

The present invention concerns erdafitinib for use in the treatment of cancer in a cancer patient, wherein erdafitinib is administered in an amount of 8 mg daily, in particular once daily, on a continuous basis, wherein the serum phosphate levels in the cancer patient are monitored and when the serum phosphate levels are <5.5 mg/dL, the amount of erdafitinib administered daily, preferably once daily, on a continuous basis, is increased to 9 mg. When the serum phosphate levels range from and including 5.5 mg/dL to <7 mg/dL, the patient remains on the 8 mg daily continuous treatment. When the serum phosphate levels are ≥7 mg/dL, the treatment is interrupted temporarily, in particular erdafitinib treatment is interrupted until serum phosphate levels are again <7 mg/dL, or the daily continuous dose is adjusted to <8 mg, in particular the treatment is interrupted temporarily, in particular until serum phosphate levels are <5.5 mg/dL. In an embodiment, the levels of serum phosphate are measured on a treatment day during the first cycle of erdafitinib treatment, in particular on day 14±2 days, more in particular on day 14, of erdafitinib administration. In an embodiment, when the serum phosphate levels are ≥7 mg/dL, the treatment is interrupted temporarily until serum phosphate levels are <5.5 mg/dL and then erdafitinib treatment is re-started with 8 mg daily, in particular once daily, on a continuous basis. In an embodiment, serum phosphate levels during further erdafitinib administration may be managed according to Table 3.

The present invention concerns erdafitinib for use in the treatment of cancer in a cancer patient, wherein erdafitinib is administered in an amount of 8 mg daily, in particular once daily, on a continuous basis, wherein the serum phosphate levels in the cancer patient are monitored and when the serum phosphate levels are <7 mg/dL or when the serum phosphate levels range from and including 7 mg/dL to ≤9 mg/dL, the amount of erdafitinib administered daily, preferably once daily, on a continuous basis, is increased to 9 mg. When the serum phosphate levels range from and including 7 mg/dL to ≤9 mg/dL, concurrent treatment with a phosphate binder, such as for example sevelamer, may be initiated. In an embodiment, concurrent treatment with a phosphate binder, such as for example sevelamer, is initiated. When the serum phosphate levels are elevated >9 mg/dL, the treatment is interrupted temporarily, in particular erdafitinib treatment is interrupted until serum phosphate levels are again <7 mg/dL, and, upon serum phosphate being below 7 mg/dL, the daily continuous dose is adjusted to the same or a lower daily dose. In an embodiment, the levels of serum phosphate are measured on a treatment day during the first cycle of erdafitinib treatment, in particular on day 14±2 days, more in particular on day 14, of erdafitinib administration. In an embodiment, when the serum phosphate levels are >9 mg/dL, the treatment is interrupted temporarily until serum phosphate levels are <7 mg/dL and then erdafitinib treatment is re-started with 8 mg daily, in particular once daily, on a continuous basis.

In an embodiment, serum phosphate levels during further erdafitinib administration may be managed according to Table 4.

The present invention concerns erdafitinib for use in the treatment of cancer in a cancer patient, wherein erdafitinib is administered in an amount of 8 mg daily, in particular once daily, on a continuous basis, wherein the serum phosphate levels in the cancer patient are monitored and early onset toxicity linked to FGFR inhibitors in general or to erdafitinib specifically shown by the cancer patient is monitored, and when the serum phosphate levels are <5.5 mg/dL and no early onset toxicity is shown, the amount of erdafitinib administered daily, preferably once daily, on a continuous basis, is increased to 9 mg. When the serum phosphate levels range from and including 5.5 mg/dL to <7 mg/dL and no early onset toxicity is shown, the patient remains on the 8 mg daily continuous treatment. When the serum phosphate levels are ≥7 mg/dL, the treatment is interrupted temporarily, in particular erdafitinib treatment is interrupted until serum phosphate levels are again <7 mg/dL, or the daily continuous dose is adjusted to <8 mg, in particular the treatment is interrupted temporarily, in particular until serum phosphate levels are <5.5 mg/dL. In an embodiment, the levels of serum phosphate are measured on a treatment day during the first cycle of erdafitinib treatment, in particular on day 14±2 days, more in particular on day 14, of erdafitinib administration. In an embodiment, when the serum phosphate levels are ≥7 mg/dL, the treatment is interrupted temporarily until serum phosphate levels are <5.5 mg/dL and then erdafitinib treatment is re-started with 8 mg daily, in particular once daily, on a continuous basis.

In an embodiment, serum phosphate levels during further erdafitinib administration may be managed according to Table 3.

The present invention concerns erdafitinib for use in the treatment of cancer in a cancer patient, wherein erdafitinib is administered in an amount of 8 mg daily, in particular once daily, on a continuous basis, wherein the serum phosphate levels in the cancer patient are monitored and early onset toxicity linked to FGFR inhibitors in general or to erdafitinib specifically shown by the cancer patient is monitored, and when the serum phosphate levels are <7 mg/dL or when the serum phosphate levels range from and including 7 mg/dL to ≤9 mg/dL, the amount of erdafitinib administered daily, preferably once daily, on a continuous basis, is increased to 9 mg. When the serum phosphate levels range from and including 7 mg/dL to ≤9 mg/dL, concurrent treatment with a phosphate binder, such as for example sevelamer, may be initiated. In an embodiment, concurrent treatment with a phosphate binder, such as for example sevelamer, is initiated. When the serum phosphate levels are elevated ≤9 mg/dL, the treatment is interrupted temporarily, in particular erdafitinib treatment is interrupted until serum phosphate levels are again <7 mg/dL, and, upon serum phosphate being below 7 mg/dL, the daily continuous dose is adjusted to the same or a lower daily dose. In an embodiment, the levels of serum phosphate are measured on a treatment day during the first cycle of erdafitinib treatment, in particular on day 14±2 days, more in particular on day 14, of erdafitinib administration. In an embodiment, when the serum phosphate levels are >9 mg/dL, the treatment is interrupted temporarily until serum phosphate levels are <7 mg/dL and then erdafitinib treatment is re-started with 8 mg daily, in particular once daily, on a continuous basis. In an embodiment, serum phosphate levels during further erdafitinib administration may be managed according to Table 4.

The present invention concerns erdafitinib for use in the treatment of cancer in a cancer patient, wherein erdafitinib is administered in an amount of 9 mg daily, in particular once daily, on a continuous basis, when the serum phosphate levels of said patient are <5.5 mg/dL while being on a treatment with erdafitinib 8 mg daily, in particular once daily, on a continuous basis. In an embodiment, the levels of serum phosphate are measured on a treatment day during the first cycle of erdafitinib treatment, in particular on day 14±2 days, more in particular on day 14, of erdafitinib administration. In an embodiment, serum phosphate levels during further erdafitinib administration may be managed according to Table 3.

The present invention concerns erdafitinib for use in the treatment of cancer in a cancer patient, wherein erdafitinib is administered in an amount of 9 mg daily, in particular once daily, on a continuous basis, when the serum phosphate levels of said patient are <7 mg/dL or when the serum phosphate levels range from and including 7 mg/dL to ≤9 mg/dL, while being on a treatment with erdafitinib 8 mg daily, in particular once daily, on a continuous basis. When the serum phosphate levels range from and including 7 mg/dL to ≤9 mg/dL, concurrent treatment with a phosphate binder, such as for example sevelamer, may be initiated. In an embodiment, concurrent treatment with a phosphate binder, such as for example sevelamer, is initiated. The levels of serum phosphate are measured on a treatment day during the first cycle of erdafitinib treatment, in particular on day 14±2 days, more in particular on day 14, of erdafitinib administration. In an embodiment, serum phosphate levels during further erdafitinib administration may be managed according to Table 4.

The present invention concerns erdafitinib for use in the treatment of cancer in a cancer patient, wherein erdafitinib is administered in an amount of 9 mg daily, in particular once daily, on a continuous basis, when the serum phosphate levels of said patient are <5.5 mg/dL and no early onset toxicity is shown while being on a treatment with erdafitinib 8 mg daily, in particular once daily, on a continuous basis. In an embodiment, the levels of serum phosphate are measured on a treatment day during the first cycle of erdafitinib treatment, in particular on day 14±2 days, more in particular on day 14, of erdafitinib administration.

In an embodiment, serum phosphate levels during further erdafitinib administration may be managed according to Table 3.

The present invention concerns erdafitinib for use in the treatment of cancer in a cancer patient, wherein erdafitinib is administered in an amount of 9 mg daily, in particular once daily, on a continuous basis, when the serum phosphate levels of said patient are <7 mg/dL or when the serum phosphate levels range from and including 7 mg/dL to ≤9 mg/dL, and no early onset toxicity is shown while being on a treatment with erdafitinib 8 mg daily, in particular once daily, on a continuous basis. When the serum phosphate levels range from and including 7 mg/dL to ≤9 mg/dL and no early onset toxicity is shown, concurrent treatment with a phosphate binder, such as for example sevelamer, may be initiated. In an embodiment, concurrent treatment with a phosphate binder, such as for example sevelamer, is initiated. In an embodiment, the levels of serum phosphate are measured on a treatment day during the first cycle of erdafitinib treatment, in particular on day 14±2 days, more in particular on day 14, of erdafitinib administration. In an embodiment, serum phosphate levels during further erdafitinib administration may be managed according to Table 4.

In an embodiment of the invention, the serum phosphate levels (to determine whether the amount of erdafitinib can be increased from 8 mg daily to 9 mg daily) are assessed when steady state levels of erdafitinib plasma concentration and serum phosphate are reached.

In an embodiment of the invention, the serum phosphate levels to determine whether the amount of erdafitinib can be increased from 8 mg daily to 9 mg daily are assessed at a treatment day during the first cycle of erdafitinib treatment, in particular at approximately day 14±2 days of erdafitinib treatment, in particular at day 14 of erdafitinib treatment (day 14 of cycle 1 of erdafitinib treatment). In an embodiment a cycle is 21 days. In an embodiment a cycle is 28 days.

The daily amount of erdafitinib as mentioned herein can be administered via one pharmaceutical composition or via more than one pharmaceutical composition. The medicament as mentioned herein can comprise one pharmaceutical composition or more than one pharmaceutical composition. In an embodiment, the 8 mg dose of erdafitinib can be administered as 2 formulations, in particular 2 tablets, each comprising 4 mg of erdafitinib. In an embodiment, the 9 mg dose of erdafitinib can be administered as 3 formulations, in particular 3 tablets, each comprising 3 mg of erdafitinib.

The present invention concerns a method for the treatment of cancer, which method comprises
  a) administering to a subject in need thereof, in particular a cancer patient, 8 mg of erdafitinib daily, in particular once daily, on a continuous basis;
  b) measuring the serum phosphate levels of the subject on a treatment day during the first cycle of erdafitinib treatment, in particular on day 14±2 days, more in particular on day 14, of erdafitinib administration;
  c-1) when the serum phosphate levels are <5.5 mg/dL, erdafitinib is administered in an amount of 9 mg daily, in particular once daily, on a continuous basis;
  c-2) when the serum phosphate levels range from and including 5.5 mg/dL to <7 mg/dL, erdafitinib is further administered in an amount of 8 mg daily, in particular once daily, on a continuous basis;
  c-3) when the serum phosphate levels are ≥7 mg/dL, the erdafitinib treatment is interrupted temporarily until serum phosphate levels are <5.5 mg/dL and then erdafitinib treatment is re-started with 8 mg daily, in particular once daily, on a continuous basis.

In an embodiment, serum phosphate levels during further erdafitinib administration may be managed according to Table 3.

The present invention concerns a method for the treatment of cancer, which method comprises
  a) administering to a subject in need thereof, in particular a cancer patient, 8 mg of erdafitinib daily, in particular once daily, on a continuous basis;
  b) measuring the serum phosphate levels of the subject on a treatment day during the first cycle of erdafitinib treatment, in particular on day 14±2 days, more in particular on day 14, of erdafitinib administration;
  c-1) when the serum phosphate levels are <7 mg/dL or when the serum phosphate levels range from and including 7 mg/dL to ≤9 mg/dL, erdafitinib is administered in an amount of 9 mg daily, in particular once daily, on a continuous basis; and when the serum phosphate levels range from and including 7 mg/dL to ≤9 mg/dL, concurrent treatment with a phosphate binder, such as for example sevelamer, is optionally initiated;
  c-2) when the serum phosphate levels are >9 mg/dL, the erdafitinib treatment is interrupted temporarily until serum phosphate levels are <7 mg/dL and then erdafitinib treatment is re-started with 8 mg daily, in particular once daily, on a continuous basis.

In an embodiment, serum phosphate levels during further erdafitinib administration may be managed according to Table 4.

The present invention concerns a method for the treatment of cancer, which method comprises
  a) administering to a subject in need thereof, in particular a cancer patient, 8 mg of erdafitinib daily, in particular once daily, on a continuous basis;
  b) measuring the serum phosphate levels of the subject on a treatment day during the first cycle of erdafitinib treatment, in particular on day 14±2 days, more in particular on day 14, of erdafitinib administration;
  c-1) when the serum phosphate levels are <5.5 mg/dL and no early onset toxicity is shown, erdafitinib is administered in an amount of 9 mg daily, in particular once daily, on a continuous basis;
  c-2) when the serum phosphate levels range from and including 5.5 mg/dL to <7 mg/dL and no early onset toxicity is shown, erdafitinib is further administered in an amount of 8 mg daily, in particular once daily, on a continuous basis; c-3) when the serum phosphate levels are ≥7 mg/dL and no early onset toxicity is shown, the erdafitinib treatment is interrupted temporarily until serum phosphate levels are <5.5 mg/dL and then erdafitinib treatment is re-started with 8 mg daily, in particular once daily, on a continuous basis.

In an embodiment, serum phosphate levels during further erdafitinib administration may be managed according to Table 3.

The present invention concerns a method for the treatment of cancer, which method comprises
   a) administering to a subject in need thereof, in particular a cancer patient, 8 mg of erdafitinib daily, in particular once daily, on a continuous basis;
   b) measuring the serum phosphate levels of the subject on a treatment day during the first cycle of erdafitinib treatment, in particular on day 14±2 days, more in particular on day 14, of erdafitinib administration;
   c-1) when the serum phosphate levels are <7 mg/dL and no early onset toxicity is shown or when the serum phosphate levels range from and including 7 mg/dL to ≤9 mg/dL and no early onset toxicity is shown, erdafitinib is administered in an amount of 9 mg daily, in particular once daily, on a continuous basis; and when the serum phosphate levels range from and including 7 mg/dL to ≤9 mg/dL, concurrent treatment with a phosphate binder, such as for example sevelamer, is optionally initiated;
   c-2) when the serum phosphate levels are >9 mg/dL and no early onset toxicity is shown, the erdafitinib treatment is interrupted temporarily until serum phosphate levels are <7 mg/dL and then erdafitinib treatment is re-started with 8 mg daily, in particular once daily, on a continuous basis.

In an embodiment, serum phosphate levels during further erdafitinib administration may be managed according to Table 4.

The present invention concerns the use of erdafitinib for the manufacture of a medicament for the treatment of cancer in a cancer patient, wherein
   a) the medicament comprises erdafitinib in an amount of 8 mg and wherein the medicament is for daily, in particular once daily, administration on a continuous basis;
   b) the serum phosphate levels of the patient are measured on a treatment day during the first cycle of erdafitinib treatment, in particular on day 14±2 days, more in particular on day 14, of erdafitinib administration;
   c-1) when the serum phosphate levels are <5.5 mg/dL, the amount of erdafitinib in the medicament for daily, in particular once daily, administration on a continuous basis is increased to 9 mg;
   c-2) when the serum phosphate levels range from and including 5.5 mg/dL to <7 mg/dL, the patient remains on the 8 mg daily, in particular once daily, continuous treatment;
   c-3) when the serum phosphate levels are ≥7 mg/dL, the erdafitinib treatment is interrupted temporarily until serum phosphate levels are <5.5 mg/dL and then erdafitinib treatment is re-started with 8 mg daily, in particular once daily, on a continuous basis.

In an embodiment, serum phosphate levels during further erdafitinib administration may be managed according to Table 3.

The present invention concerns the use of erdafitinib for the manufacture of a medicament for the treatment of cancer in a cancer patient, wherein
   a) the medicament comprises erdafitinib in an amount of 8 mg and wherein the medicament is for daily, in particular once daily, administration on a continuous basis;
   b) the serum phosphate levels of the patient are measured on a treatment day during the first cycle of erdafitinib treatment, in particular on day 14±2 days, more in particular on day 14, of erdafitinib administration;
   c-1) when the serum phosphate levels are <7 mg/dL or when the serum phosphate levels range from and including 7 mg/dL to ≤9 mg/dL, the amount of erdafitinib in the medicament for daily, in particular once daily, administration on a continuous basis is increased to 9 mg; and when the serum phosphate levels range from and including 7 mg/dL to ≤9 mg/dL, concurrent treatment with a phosphate binder, such as for example sevelamer, is optionally initiated;
   c-2) when the serum phosphate levels are >9 mg/dL, the erdafitinib treatment is interrupted temporarily until serum phosphate levels are <7 mg/dL and then erdafitinib treatment is re-started with 8 mg daily, in particular once daily, on a continuous basis.

In an embodiment, serum phosphate levels during further erdafitinib administration may be managed according to Table 4.

The present invention concerns the use of erdafitinib for the manufacture of a medicament for the treatment of cancer in a cancer patient, wherein
   a) the medicament comprises erdafitinib in an amount of 8 mg and wherein the medicament is for daily, in particular once daily, administration on a continuous basis;
   b) the serum phosphate levels of the patient are measured on a treatment day during the first cycle of erdafitinib treatment, in particular on day 14±2 days, more in particular on day 14, of erdafitinib administration;
   c-1) when the serum phosphate levels are <5.5 mg/dL and no early onset toxicity is shown, the amount of erdafitinib in the medicament for daily, in particular once daily, administration on a continuous basis is increased to 9 mg;
   c-2) when the serum phosphate levels range from and including 5.5 mg/dL to <7 mg/dL and no early onset toxicity is shown, the patient remains on the 8 mg daily, in particular once daily, continuous treatment;
   c-3) when the serum phosphate levels are ≥7 mg/dL and no early onset toxicity is shown, the erdafitinib treatment is interrupted temporarily until serum phosphate levels are <5.5 mg/dL and then erdafitinib treatment is re-started with 8 mg daily, in particular once daily, on a continuous basis.

In an embodiment, serum phosphate levels during further erdafitinib administration may be managed according to Table 3.

The present invention concerns the use of erdafitinib for the manufacture of a medicament for the treatment of cancer in a cancer patient, wherein
   a) the medicament comprises erdafitinib in an amount of 8 mg and wherein the medicament is for daily, in particular once daily, administration on a continuous basis;
   b) the serum phosphate levels of the patient are measured on a treatment day during the first cycle of erdafitinib treatment, in particular on day 14±2 days, more in particular on day 14, of erdafitinib administration;
   c-1) when the serum phosphate levels are <7 mg/dL and no early onset toxicity is shown or when the serum phosphate levels range from and including 7 mg/dL to ≤9 mg/dL and no early onset toxicity is shown, the amount of erdafitinib in the medicament for daily, in particular once daily, administration on a continuous basis is increased to 9 mg; and when the serum phosphate levels range from and including 7 mg/dL to ≤9 mg/dL, concurrent treatment with a phosphate binder, such as for example sevelamer, is optionally initiated;

c-2) when the serum phosphate levels are >9 mg/dL and no early onset toxicity is shown, the erdafitinib treatment is interrupted temporarily until serum phosphate levels are <7 mg/dL and then erdafitinib treatment is re-started with 8 mg daily, in particular once daily, on a continuous basis.

In an embodiment, serum phosphate levels during further erdafitinib administration may be managed according to Table 4.

The present invention concerns erdafitinib for use in the treatment of cancer in a cancer patient, wherein
  a) erdafitinib is administered in an amount of 8 mg daily, in particular once daily, on a continuous basis;
  b) the serum phosphate levels of the patient are measured on a treatment day during the first cycle of erdafitinib treatment, in particular on day 14±2 days, more in particular on day 14, of erdafitinib administration;
  c-1) when the serum phosphate levels are <5.5 mg/dL, erdafitinib is administered in an amount of 9 mg daily, in particular once daily, on a continuous basis;
  c-2) when the serum phosphate levels range from and including 5.5 mg/dL to <7 mg/dL, erdafitinib is further administered in an amount of 8 mg daily, in particular once daily, on a continuous basis;
  c-3) when the serum phosphate levels are ≤7 mg/dL, the erdafitinib treatment is interrupted temporarily until serum phosphate levels are <5.5 mg/dL and then erdafitinib treatment is re-started with 8 mg daily, in particular once daily, on a continuous basis.

In an embodiment, serum phosphate levels during further erdafitinib administration may be managed according to Table 3.

The present invention concerns erdafitinib for use in the treatment of cancer in a cancer patient, wherein
  a) erdafitinib is administered in an amount of 8 mg daily, in particular once daily, on a continuous basis;
  b) the serum phosphate levels of the patient are measured on a treatment day during the first cycle of erdafitinib treatment, in particular on day 14±2 days, more in particular on day 14, of erdafitinib administration;
  c-1) when the serum phosphate levels are <7 mg/dL or when the serum phosphate levels range from and including 7 mg/dL to ≤9 mg/dL, erdafitinib is administered in an amount of 9 mg daily, in particular once daily, on a continuous basis; and when the serum phosphate levels range from and including 7 mg/dL to ≤9 mg/dL, concurrent treatment with a phosphate binder, such as for example sevelamer, is optionally initiated;
  c-2) when the serum phosphate levels are >9 mg/dL, the erdafitinib treatment is interrupted temporarily until serum phosphate levels are <7 mg/dL and then erdafitinib treatment is re-started with 8 mg daily, in particular once daily, on a continuous basis.

In an embodiment, serum phosphate levels during further erdafitinib administration may be managed according to Table 4.

The present invention concerns erdafitinib for use in the treatment of cancer in a cancer patient, wherein
  a) erdafitinib is administered in an amount of 8 mg daily, in particular once daily, on a continuous basis;
  b) the serum phosphate levels of the patient are measured on a treatment day during the first cycle of erdafitinib treatment, in particular on day 14±2 days, more in particular on day 14, of erdafitinib administration;
  c-1) when the serum phosphate levels are <5.5 mg/dL and no early onset toxicity is shown, erdafitinib is administered in an amount of 9 mg daily, in particular once daily, on a continuous basis;
  c-2) when the serum phosphate levels range from and including 5.5 mg/dL to <7 mg/dL and no early onset toxicity is shown, erdafitinib is further administered in an amount of 8 mg daily, in particular once daily, on a continuous basis;
  c-3) when the serum phosphate levels are ≥7 mg/dL and no early onset toxicity is shown, the erdafitinib treatment is interrupted temporarily until serum phosphate levels are <5.5 mg/dL and then erdafitinib treatment is re-started with 8 mg daily, in particular once daily, on a continuous basis.

In an embodiment, serum phosphate levels during further erdafitinib administration may be managed according to Table 3.

The present invention concerns erdafitinib for use in the treatment of cancer in a cancer patient, wherein
  a) erdafitinib is administered in an amount of 8 mg daily, in particular once daily, on a continuous basis;
  b) the serum phosphate levels of the patient are measured on a treatment day during the first cycle of erdafitinib treatment, in particular on day 14±2 days, more in particular on day 14, of erdafitinib administration;
  c-1) when the serum phosphate levels are <7 mg/dL and no early onset toxicity is shown or when the serum phosphate levels range from and including 7 mg/dL to ≤9 mg/dL and no early onset toxicity is shown, erdafitinib is administered in an amount of 9 mg daily, in particular once daily, on a continuous basis; and when the serum phosphate levels range from and including 7 mg/dL to ≤9 mg/dL, concurrent treatment with a phosphate binder, such as for example sevelamer, is optionally initiated;
  c-2) when the serum phosphate levels are >9 mg/dL and no early onset toxicity is shown, the erdafitinib treatment is interrupted temporarily until serum phosphate levels are <7 mg/dL and then erdafitinib treatment is re-started with 8 mg daily, in particular once daily, on a continuous basis.

In an embodiment, serum phosphate levels during further erdafitinib administration may be managed according to Table 4.

It is to be understood that the methods of treatment and uses as described herein are based on phosphate levels as a pharmacodynamic marker, but they can be modified or terminated based on toxicity. In an embodiment, treatment or uses are modified or terminated as described in Table 1.

TABLE 1

Erdafitinib dose modifications based on toxicity.

| Toxicity Grade | Action | Dose modification after resolution of adverse event |
| --- | --- | --- |
| 1 | None | Continue same dose |
| 2 | None or consider interruption | If interrupted, restart at same dose or 1 dose lower, if necessary |
| 3 | Interrupt drug | Restart at 1 or 2 doses lower or discontinue depending on recovery. |
| 4 | Interrupt drug | Discontinue |

If erdafitinib is interrupted, in particular interrupted consecutively for 1 week or longer due to drug-related toxicity, it may be reintroduced at either the same dose level or the first reduced dose level following recovery from the toxicity. In an embodiment, erdafitinib dose reductions levels are as described in Table 2. A second dose reduction may be implemented following a second occurrence of drug-related toxicity, in particular as described in Table 2.

TABLE 2

Erdafitinib dose reduction levels

| Category | No up-titration Dose | With up-titration Dose |
|---|---|---|
| Starting dose | 8 mg | 8 mg |
| Up-titration | None | 9 mg |
| 1st dose reduction | 6 mg | 8 mg |
| 2nd dose reduction | 5 mg | 6 mg |
| 3rd dose reduction | 4 mg | 5 mg |
| 4th dose reduction | stop | 4 mg |
| 5th dose reduction |  | stop |

It is to be understood that, in case treatment with or administration of erdafitinib should be discontinued, for instance if erdafitinib must be withheld for more than 28 days for a drug-related adverse event that fails to resolve to acceptable level (≤Grade 1 or back to baseline for non-hematologic toxicity) it is at the discretion of the physician to decide to continue treatment when the patient has been deriving benefit from treatment, and the physician can demonstrate that continued treatment with erdafitinib is in the best interest of the patient. If erdafitinib was dose-reduced and the adverse event that was the reason for this dose-reduction has completely resolved, the dose may be re-escalated to the next higher level if the patient was deriving benefit from treatment, and the physician can demonstrate that dose re-escalation of erdafitinib is in the best interest of the patient.

It is to be understood that patients with any grade of toxicity (Grade 1 to 4) should be provided symptomatic treatment where applicable.

In an embodiment, if treatment with erdafitinib is interrupted as described herein, and serum phosphate levels are monitored until they return to the indicated levels, the assessment of serum phosphate is done at least weekly.

In an embodiment, if treatment with erdafitinib is interrupted for hyperphosphatemia as described herein, the interruption is about 7 days, in particular is 7 days.

dose of erdafitinib, in particular measured on a treatment day during the first cycle of erdafitinib treatment, in particular on day 14±2 days, more in particular on day 14, of erdafitinib administration, phosphate levels may be further monitored during erdafitinib treatment. In an embodiment, clinical management of serum phosphate levels is done as represented in Table 3.

TABLE 3

Guidelines for management of serum phosphate elevation

| Serum Phosphate Level | Erdafitinib management |
|---|---|
| <5.5 mg/dL | Continue erdafitinib administration |
| 5.5-6.9 mg/dL | Continue erdafitinib administration |
| 7.0-9.0 mg/dL | Withhold erdafitinib administration until serum phosphate level returns to <5.5 mg/dL. Re-start treatment at the same dose level. A dose reduction may be implemented if clinically indicated |
| >9.0 mg/dL | Withhold erdafitinib treatment until serum phosphate level returns to <5.5 mg/dL. Re-start treatment at lower dose (e.g. first reduced dose level or second reduced dose level) as clinically indicated |
| >10.0 mg/dL and/or significant alteration in baseline renal function and/or Grade 3 hypocalcemia | Erdafitinib should be discontinued permanently but might, in case of the subject having clinical benefit and re-starting drug is in the best interest of the subject, be re-introduced at lower dose. |

In an embodiment, clinical management of serum phosphate levels is done as represented in Table 4.

TABLE 4

Guidelines for management of serum phosphate elevation

| Serum Phosphate Level | Erdafitinib management |
|---|---|
| <5.5 mg/dL | Continue erdafitinib administration |
| 5.5-6.9 mg/dL | Continue erdafitinib administration |
| 7.0-9.0 mg/dL | Continue erdafitinib treatment. A dose reduction may be implemented if clinically indicated. |
| >9.0 mg/dL-10 mg/dL | Withhold erdafitinib treatment until serum phosphate level returns to <7.0 mg/dL (weekly testing recommended). Re-start treatment at the same dose level. A dose reduction may be implemented if clinically indicated. |
| >10.0 mg/dL | Withhold erdafitinib treatment until serum phosphate level returns to <7.0 mg/dL (weekly testing recommended). Re-start treatment at lower dose (e.g. first reduced dose level or second reduced dose level) as clinically indicated. If hyperphosphatemia (≥10 mg/dL) for >2 weeks, erdafitinib should be discontinued permanently. |
| Significant alteration in baseline renal function or Grade 3 hypocalcemia | Erdafitinib should be discontinued permanently but might, in case of the subject having clinical benefit and re-starting drug is in the best interest of the subject, be re-introduced at lower dose. |

It is to be understood that when the serum phosphate levels are measured as a pharmacodynamic marker for determining whether or not to up-titrate the 8 mg starting It is to be understood that for managing elevated phosphate, restrictions to daily phosphate intake may be requested.

It is to be understood that for managing elevated phosphate, patients may have to take concurrently a phosphate binder, such as for example sevelamer phosphate.

Assessments of tumor responses as reported herein were performed according to Response Evaluation Criteria in Solid Tumors (RECIST) version 1.1.

The present invention also concerns a package containing an erdafitinib formulation and written information, e.g. a patient leaflet, on the dosing regimens as described herein.

In an embodiment the cancers mentioned herein are cancers mediated by a FGFR kinase.

In an embodiment the cancer is bladder cancer.

In an embodiment the cancer is hepatocellular cancer.

In an embodiment the cancer is squamous cell carcinoma.

In an embodiment, the cancer is squamous NSCLC (non-small cell lung cancer), in particular squamous NSCLC (non-small cell lung carcinoma) harboring select FGFR genetic alterations, in particular the treatment of cancer in a patient with squamous NSCLC (non-small cell lung carcinoma) harboring select FGFR genetic alterations after relapse of standard of care therapy.

In an embodiment the cancer is hepatocellular cancer harboring FGF19 amplification or overexpression.

In an embodiment the cancer is cholangiocarcinoma, in particular advanced or metastatic cholangiocarcinoma.

In an embodiment, the cancer is urothelial cancer.

In an embodiment the cancer is metastatic or surgically unresectable urothelial cancer.

In an embodiment the cancer is advanced urothelial cancer with selected FGFR gene alterations, in particular the treatment of cancer in a patient with advanced urothelial cancer with selected FGFR gene alterations who has progressed on or after one prior treatment.

In an embodiment the cancer is lung cancer, in particular non small cell lung cancer.

In an embodiment the cancer is selected from adenoid cystic carcinoma, mucoepidermoid carcinoma, follicular thyroid carcinoma, breast carcinoma, Ewing sarcoma, small round cell bone tumors, synovial sarcoma, glioblastoma multiforme, pilocytic astrocytoma, lung cancer, clear cell renal cell carcinoma, bladder cancer, prostate cancer, ovarian cancer, colorectal cancer.

In an embodiment the cancer is multiple myeloma, in particular t(4;14) translocation positive multiple myeloma.

In an embodiment, the cancer is non-muscle-invasive bladder cancer, in particular non-muscle-invasive bladder cancer with FGFR genomic alterations (e.g. translocations, fusions and/or mutations).

In an embodiment the cancer is esophageal cancer or head and neck cancer.

In an embodiment the cancer is gastric cancer.

In an embodiment, the cancers mentioned herein are cancers harboring FGFR genomic alterations (e.g. translocations, fusions and/or mutations), in particular cancers harboring FGFR genomic alterations (e.g. translocations, fusions and/or mutations) sensitive to erdafitinib, e.g. bladder cancer with FGFR genomic alterations (e.g. translocations, fusions and/or mutations), or urothelial cancer with FGFR genomic alterations (e.g. translocations, fusions and/or mutations) or metastatic or surgically unresectable urothelial cancer with FGFR genomic alterations (e.g. translocations, fusions and/or mutations) or cholangiocarcinoma with FGFR genomic alterations (e.g. translocations, fusions and/or mutations) or advanced or metastatic cholangiocarcinoma with FGFR genomic alterations (e.g. translocations, fusions and/or mutations).

In an embodiment the cancers mentioned herein are cancers harboring alterations selected from the following fusions FGFR3:TACC3 v1; FGFR3:TACC3 v3; FGFR3: TACC3 Intron; FGFR3:BAIAP2L1; FGFR2:AFF3; FGFR2: BICC1; FGFR2:CASP7; FGFR2:CCDC6 and FGFR2: OFD1.

In an embodiment, the cancers mentioned herein are cancers with a FGFR3-TACC3 fusion or translocation, e.g. bladder cancer with FGFR3-TACC3 translocation, or urothelial cancer with FGFR3-TACC3 translocation, or metastatic or surgically unresectable urothelial cancer with FGFR3-TACC3 translocation.

In an embodiment the cancers mentioned herein are cancers harboring alterations selected from the following FGFR3 gene mutations: FGFR3 R248C, FGFR3 S249C, FGFR3 G370C, FGFR3 Y373C.

In an embodiment the cancers mentioned herein are bladder cancer or urothelial cancer or metastatic or surgically unresectable urothelial cancer harboring at least one of the following FGFR3 gene mutations: FGFR3 R248C, FGFR3 S249C, FGFR3 G370C, FGFR3 Y373C.

In an embodiment, the uses for or the methods of treatment of cancer in a subject in need thereof, in particular a cancer patient, as mentioned herein is the use for or the treatment of a patient with metastatic or surgically unresectable urothelial carcinoma whose tumors harbor select FGFR genomic alterations, who has failed during or following at least one line of prior systemic chemotherapy, or within 12 months of neoadjuvant or adjuvant chemotherapy, or chemo-naïve but ineligible for cisplatin.

In an embodiment, the uses for or the methods of treatment of cancer in a subject in need thereof, in particular a cancer patient, as mentioned herein, is the use for or the treatment of a patient with luminal cluster I subtype urothelial cancer.

In an embodiment erdafitinib is administered as a pharmaceutically acceptable salt.

In a preferred embodiment erdafitinib (base) is administered.

In an embodiment erdafitinib is administered as a pharmaceutically acceptable salt in an amount corresponding to 8 mg base equivalent or corresponding to 9 mg base equivalent.

The salts can be prepared by for instance reacting erdafitinib with an appropriate acid in an appropriate solvent.

Acid addition salts may be formed with acids, both inorganic and organic. Examples of acid addition salts include salts formed with an acid selected from the group consisting of acetic, hydrochloric, hydriodic, phosphoric, nitric, sulphuric, citric, lactic, succinic, maleic, malic, isethionic, fumaric, benzenesulphonic, toluenesulphonic, methanesulphonic (mesylate), ethanesulphonic, naphthalenesulphonic, valeric, acetic, propanoic, butanoic, malonic, glucuronic and lactobionic acids. Another group of acid addition salts includes salts formed from acetic, adipic, ascorbic, aspartic, citric, DL-Lactic, fumaric, gluconic, glucuronic, hippuric, hydrochloric, glutamic, DL-malic, methanesulphonic, sebacic, stearic, succinic and tartaric acids.

In an embodiment, erdafitinib is administered in the form of a solvate. As used herein, the term "solvate" means a physical association of erdafitinib with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. The term "solvate" is intended to encompass both solution-phase and isolatable solvates. Non-limiting examples of solvents that may form solvates include water, isopropanol, ethanol, methanol, DMSO, ethyl acetate, acetic acid or ethanolamine and the like.

Solvates are well known in pharmaceutical chemistry. They can be important to the processes for the preparation of a substance (e.g. in relation to their purification, the storage of the substance (e.g. its stability) and the ease of handling of the substance and are often formed as part of the isolation or purification stages of a chemical synthesis. A person skilled in the art can determine by means of standard and long used techniques whether a hydrate or other solvate has formed by the isolation conditions or purification conditions used to prepare a given compound. Examples of such techniques include thermogravimetric analysis (TGA), differential scanning calorimetry (DSC), X-ray crystallography (e.g. single crystal X-ray crystallography or X-ray powder diffraction) and Solid State NMR (SS-NMR, also known as Magic Angle Spinning NMR or MAS-NMR). Such techniques are as much a part of the standard analytical toolkit of the skilled chemist as NMR, IR, HPLC and MS. Alternatively the skilled person can deliberately form a solvate using crystallisation conditions that include an amount of the solvent required for the particular solvate. Thereafter the standard methods described above, can be used to establish whether solvates had formed. Also encompassed are any complexes (e.g. inclusion complexes or clathrates with compounds such as cyclodextrins, or complexes with metals).

In an embodiment, the treatment cycle as used herein is a 28 day cycle.

In an embodiment, the patient, in particular the cancer patient, or the subject in need of erdafitinib treatment, as used herein, is a human.

The term "about" as used herein in connection with a numerical value is meant to have its usual meaning in the context of the numerical value. Where necessary the word "about" may be replaced by the numerical value ±10%, or ±5%, or ±2%, or ±1%.

All documents cited herein are incorporated by reference in their entirety.

EXAMPLES

Ongoing Phase 2, Multi Center, Open-Label Study (NCT02365597)

A Phase 2, multicenter, open-label study is being conducted to evaluate the efficacy and safety of erdafitinib in subjects with metastatic or surgically unresectable urothelial cancer harboring select FGFR genetic alterations (FGFR translocations or mutations).

The study comprises a Screening Phase (molecular screening at any time prior to first dose and study screening within 30 days of first dose), a treatment phase, and a post-treatment follow-up phase. The treatment phase comprises the period from first dose until the end-of-treatment visit. The follow-up phase will extend until the subject has died, withdraws consent, is lost to follow-up, or the end of study, whichever comes first. Study treatment is administered on 28-day cycles. Prior to interim analysis 1, there were 2 treatment regimens. Patients were randomized 1:1 to 28 day cycles to the following 2 regimens until a regimen was selected for further study: Regimen 1 (10 mg once daily intermittent (7 days on/7 days); Regimen 2 (6 mg once daily continuous). Following interim analysis 1 and based on the results of pharmacokinetic and pharmacodynamic modeling linking erdafitinib dose regimen and serum phosphate levels, the protocol was amended to increase the starting dose to 8 mg/day continuous dosing (Regimen 3) with an up-titration to 9 mg/day at day 14 in patients who did not reach target serum phosphate levels at this timepoint (patients with serum phosphate levels <5.5 mg/dL) and in whom no treatment-related adverse events were observed). Dose reductions based on observed toxicity (treatment-related adverse events (TRAEs)) was foreseen in the protocol. See FIG. 1 for the Phase 2 study scheme.

Patients

Included patients were adults with measurable urothelial cancer per Response Evaluation Criteria in Solid Tumors version 1.1.

Patients were required to have at least 1 FGFR2/FGFR3 mutation or fusion per central lab testing of RNA from formalin-fixed, paraffin-embedded tumor samples, using a custom assay.

Patients had progressed during or following at least 1 line of prior systemic chemotherapy or less than 12 months of neoadjuvant or adjuvant chemotherapy.

Chemotherapy-naïve patients who were ineligible for cisplatin based on protocol criteria were allowed. Ineligibility for cisplatin was based on impaired renal function, defined as 1) glomerular filtration rate <60 mL/min/1.73 $m^2$ by 24-hour urine measurement; 2) calculated by Cockcroft-Gault; or 3) grade 2 or higher peripheral neuropathy (Common Terminology Criteria for Adverse Events [CTCAE] version 4.0 (National Cancer Institute. CTCAE v4.0. NCI, NIH, DHHS. May 29, 2009. NIH publication #09-7473: 2009).

Eastern Cooperative Oncology Group (ECOG) performance status 0-2 was required.

There was no limit on the number of prior lines of treatment.

Prior immunotherapy (eg, treatment with a PD-L1/PD-1 inhibitor) was allowed.

Patients were required to have adequate bone marrow, liver and renal (creatinine clearance ≥40 mL/min) function.

Patients with phosphate levels persistently above the upper limit of normal despite medical management, uncontrolled cardiovascular disease, brain metastases, known hepatitis B or C, or known HIV were excluded.

End Points

The primary end point of this ongoing study is Objective Response Rate to the selected regimen (Regimen 3).

Secondary end points include progression-free survival (PFS), duration of response (DoR), Overall Survival, safety, predictive biomarker evaluation, and pharmacokinetics.

Assessments

Patients were assessed for efficacy using radiographic imaging performed within 30 days of screening, once every 6 weeks for the first 3 months, once every 12 weeks for the next 9 months, then once every 4 to 6 months until disease progression. Tumor responses were assessed by investigators according to RECIST version 1.1 (Eisenhauer E A et al., Eur J Cancer, 2009, 45(2), 228-247).

Safety was assessed continuously by the investigator and based on medical review of AE reports and the results of vital sign measurements, physical examinations, clinical laboratory tests, ECOG performance status, and other safety evaluations.

Results

Baseline characteristics and efficacy data are presented for 170 patients enrolled between May 7, 2015, and Jun. 10, 2017, and considered response evaluable according to RECIST 1.1 (Table 5).

Safety data are presented for the safety population (N=207, enrolled between May 7, 2015, and Dec. 5, 2017), defined as patients who received at least 1 dose of study treatment. As of Dec. 5, 2017, the median treatment duration was 4.2 months, and patients had received a median of 5 cycles of erdafitinib.

During the screening phase, 21% of patients had an FGFR mutation or fusion meeting inclusion criteria.

Across dose regimens, 89% had progressed following at least 1 line of prior treatment with systemic chemotherapy.

TABLE 5

| Baseline Characteristics[a] | | | |
|---|---|---|---|
| | Regimen 1<br>10 mg intermittent<br>dose<br>(n = 33) | Regimen 2<br>6 mg<br>continuous dose<br>(n = 78) | Regimen 3<br>8 mg<br>continuous dose<br>(n = 59) |
| Age, median (range) | 68 (53-88) | 65 (42-88) | 67 (36-87) |
| ECOG performance status | | | |
| 0 | 11 (33) | 22 (28) | 35 (59) |
| 1 | 15 (46) | 41 (53) | 20 (34) |
| 2 | 7 (21) | 15 (19) | 4 (7) |
| Pretreatment | | | |
| Chemo-refractory[b] | 29 (88) | 73 (94) | 50 (85) |
| Chemo-naïve[c] | 4 (12) | 5 (6) | 9 (15) |
| Prior immunotherapy | 3 (9) | 8 (10) | 11 (19) |
| Number of lines of prior treatment | | | |
| 0 | 3 (9) | 6 (8) | 8 (14) |
| 1 | 14 (42) | 34 (44) | 27 (46) |
| 2 | 11 (33) | 25 (32) | 18 (31) |
| 3 | 4 (12) | 11 (14) | 5 (8) |
| >3 | 1 (3) | 2 (3) | 1 (2) |
| Visceral metastases | | | |
| Present | 24 (73) | 60 (77) | 45 (76) |
| Absent | 9 (27) | 18 (23) | 14 (24) |
| Creatinine clearance rate | | | |
| 40-59 mL/min | 12 (36) | 40 (51) | 32 (54) |
| ≥60 mL/min | 21 (64) | 38 (49) | 27 (46) |
| Any FGFR alteration[d] | 33 (100) | 78 (100) | 59 (100) |
| FGFR2/3 fusion[d] | 6 (18) | 15 (21) | 20 (34) |
| FGFR3 mutation[d] | 30 (91) | 66 (85) | 39 (66) |
| Both FGFR mutation and fusion | 3 (9) | 4 (5) | 0 |

All values are n (%) unless noted.

[a]Data from all patients as of Jun. 10, 2017, data cutoff (n = 170).
[b]Chemotherapy-refractory patients were those who had progressed during or following ≥1 line of prior systemic chemotherapy or within 12 months of adjuvant or neoadjuvant chemotherapy.
[c]Chemotherapy-naive patients were those who were ineligible for cisplatin. Ineligibility for cisplatin was based on impaired renal function defined as 1) glomerular filtration rate <60 mL/min/1.73 m2 by 24-hour urine measurement; 2) calculated by Cockcroft-Gault; or 3) grade 2 or higher peripheral neuropathy (CTCAE version 4.0).
[d]Patients could have more than 1 FGFR alteration.

Figure 2:
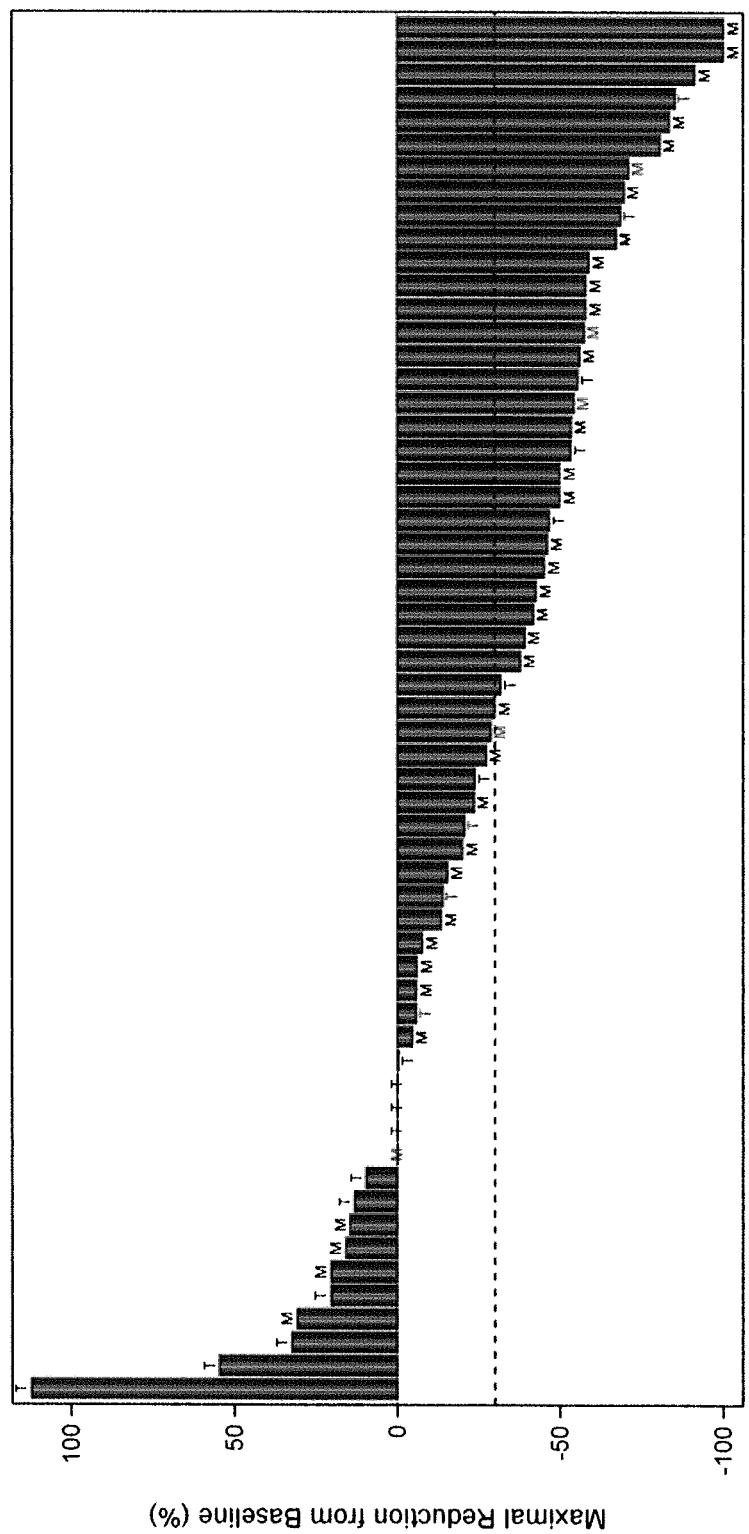
FIG. 2 represents a Waterfall plot of maximum percentage reduction from baseline in sum of target lesion diameters among patients treated with the regimen of 8 mg continuous erdafitinib (Regimen 3 of the phase 2 study (FIG. 1)). M, FGFR mutation; T, FGFR translocation.

Across all dose regimens, the confirmed Objective Response Rate was 35% (95% CI, 28%-43%), with the highest rate among patients who were treated with 8 mg/d continuous erdafitinib in Regimen 3 (Table 6). The confirmed disease control rate was 76% among all patients. The majority of patients treated with 8 mg/d continuous erdafitinib had reduction in tumor burden (44/59 [75%] had reduction in the sum of target lesion diameters; FIG. 2). Median Progression Free Survival was 5.1 months and was most prolonged among patients who were treated with 8 mg/d continuous erdafitinib in Regimen 3 (Table 6). Median duration of response in the 8 mg/d continuous erdafitinib group (Regimen 3) was 5.4 months, and many responses are ongoing (Table 6).

TABLE 6

| Antitumor Activity of 3 Dose Regimens of Erdafitiniba | | | |
|---|---|---|---|
| | Regimen 1<br>10 mg<br>intermittent<br>dose<br>(n = 33) | Regimen 2<br>6 mg<br>continuous<br>dose<br>(n = 78) | Regimen 3<br>8 mg<br>continuous dose<br>(n = 59) |
| ORR, confirmed, n (%) | 8 (24) | 27 (35) | 25 (42) |
| Complete response | 2 (6) | 2 (3) | 3 (5) |
| Partial response | 6 (18) | 25 (32) | 22 (37) |
| Stable disease | 16 (49) | 30 (39) | 23 (39) |
| P value of ORR compared with ORR in Regimen 3 | 0.354 | 0.082 | — |
| Disease control rate, confirmed, n (%) | 24 (73) | 57 (73) | 48 (81) |
| Duration of response, median, months | 12.6 | 4.9 | 5.4 |
| Follow-up for survival, median, months | 18.4 | 15.5 | 8.8 |
| Progression-free survival, median, months | 4.0 | 5.1 | 5.6 |

[a]Data from all patients as of Jun. 10, 2017, data cutoff (n = 170).
ORR, confirmed = Confirmed Objective Response Rate = Confirmed Complete Response + Confirmed Partial Response.
Disease Control Rate, confirmed = Confirmed Complete Response + Confirmed Partial Response + Stable disease Time to Response The median time to response in the subset of 59 patients on Regimen 3 was 1.41 months, with a range of 1.1 to 5.5 months.

Across all dose regimens, 94% (n=195) of patients reported TRAEs; most of these were grade 1 or 2 (Table 7).

TRAEs associated with the class of FGFR inhibitors were typically grade 1 or 2; across all dose regimens, 2 patients reported retinopathy (grade 2 [n=1] and grade 3 [n=1]). Across all dose regimens, 22 (11%) patients discontinued as the result of TRAEs. The most common TRAEs leading to treatment discontinuation were asthenia, dry mouth, and palmar-plantar erythrodysaesthesia syndrome.

TABLE 7

TRAEs Reported in ≥10% of Patients in Regimen 3[a]

|  | Regimen 1 10 mg intermittent dose (n = 33) | | Regimen 2 6 mg continuous dose (n = 78) | | Regimen 3 8 mg continuous dose (n = 96) | |
| --- | --- | --- | --- | --- | --- | --- |
|  | Any grade | Grade ≥ 3 | Any grade | Grade ≥ 3 | Any grade | Grade ≥ 3 |
| AEs, n (%) | | | | | | |
| Hyperphosphatemia | 15 (46) | 0 | 48 (62) | 0 | 66 (69) | 2 (2) |
| Stomatitis | 16 (49) | 1 (3) | 32 (41) | 7 (9) | 45 (47) | 8 (8) |
| Diarrhea | 13 (39) | 1 (3) | 34 (44) | 0 | 40 (42) | 3 (3) |
| Dry mouth | 14 (42) | 0 | 31 (40) | 2 (3) | 40 (42) | 0 |
| Dysgeusia | 10 (30) | 0 | 10 (13) | 0 | 32 (33) | 1 (1) |
| Dry skin | 7 (21) | 0 | 17 (22) | 0 | 26 (27) | 0 |
| Decreased appetite | 7 (21) | 0 | 18 (23) | 2 (3) | 23 (24) | 0 |
| Alopecia | 3 (9) | 0 | 7 (9) | 0 | 22 (23) | 0 |
| Fatigue | 4 (12) | 0 | 14 (18) | 1 (1) | 19 (20) | 1 (1) |
| Dry eye | 2 (6) | 0 | 2 (3) | 1 (1) | 17 (18) | 0 |
| Vision blurred | 4 (12) | 0 | 5 (6) | 1 (1) | 15 (16) | 0 |
| Palmar-plantar erythrodysaesthesia syndrome | 2 (6) | 0 | 12 (15) | 0 | 15 (16) | 4 (4) |
| Paronychia | 2 (6) | 0 | 11 (14) | 0 | 14 (15) | 3 (3) |
| Asthenia | 6 (18) | 2 (6) | 12 (15) | 4 (5) | 13 (14) | 3 (3) |
| Nail dystrophy | 2 (6) | 0 | 7 (9) | 0 | 12 (13) | 3 (3) |
| Lacrimation increased | 4 (12) | 0 | 11 (14) | 0 | 8 (8) | 0 |
| Onycholysis | 5 (15) | 0 | 13 (17) | 5 (6) | 10 (10) | 1 (1) |
| FGFR inhibitor class effects (summed terms | | | | | | |
| Eye AEs | 14 (42) | 1 (3) | 27 (35) | 2 (3) | 55 (57) | 5 (5) |
| Skin and subcutaneous AEs | 14 (42) | 1 (3) | 47 (60) | 5 (6) | 63 (66) | 13 (14) |

[a]Data from all patients as of Dec. 5, 2017, data cutoff (N = 207).

33% (n=69) of patients reported grade 3 TRAEs, 0.5% (n=1) of patients reported grade 4 TRAEs, and there were no treatment-related deaths.

AEs were manageable.

Prophylaxis recommendations for key AEs related to treatment with erdafitinib:

To reduce risk of hyperphosphatemia, a low-phosphate diet was recommended for all patients (600-800 mg of dietary phosphate intake per day).

To reduce risk of skin effects, the application of alcohol-free, emollient moisturizing cream and avoidance of unnecessary exposure to sunlight, soap, perfumed products, and hot baths was recommended.

To reduce risk of nail effects, it was recommended that patients keep their fingers and toes cleaned and nails trimmed.

Management

Hyperphosphatemia (>5.5 mg/dL) was managed with a phosphate-binding agent when medically warranted.

Dry skin was managed with additional topical ointments such as ammonium lactate, salicylic acid, or zinc oxide creams.

Nail effects were managed with topical nail strengthener; antibiotics or silver nitrate were applied in severe cases.

The invention claimed is:

1. A method for the treatment of urothelial cancer harboring at least one FGFR genomic alteration, which method comprises:
   a) administering to a subject in need thereof, 8 mg of erdafitinib daily on a continuous basis;
   b) measuring the serum phosphate levels of the subject on a treatment day during the first cycle of erdafitinib treatment; and
   c-1) when the serum phosphate levels are <5.5 mg/dL, erdafitinib is administered in an amount of 9 mg daily, on a continuous basis; or
   c-2) when the serum phosphate levels range from and including 5.5 mg/dL to <7 mg/dL, erdafitinib is further administered in an amount of 8 mg daily, on a continuous basis; or
   c-3) when the serum phosphate levels are ≥7 mg/dL, the erdafitinib treatment is interrupted temporarily.

2. The method of claim 1, wherein the 8 mg of erdafitinib is administered once daily.

3. The method of claim 1, wherein the serum phosphate levels of the subject measured on a treatment day during the first cycle of erdafitinib treatment are measured on day 14±2 days of erdafitinib administration.

4. The method of claim 3, wherein the serum phosphate levels of the subject measured on a treatment day during the first cycle of erdafitinib treatment are measured on day 14 of erdafitinib administration.

5. The method of claim 1, wherein the 9 mg of erdafitinib is administered once daily.

6. The method of claim 1, wherein when the serum phosphate levels are ≥7 mg/dL, the erdafitinib treatment is interrupted temporarily until serum phosphate levels are <5.5 mg/dL.

7. The method of claim 1, wherein when the serum phosphate levels range from 7 mg/dL to ≤9 mg/dL, the erdafitinib treatment is interrupted temporarily until serum phosphate levels are <5.5 mg/dL and then erdafitinib treatment is re-started with 8 mg daily on a continuous basis.

8. The method of claim 1, wherein when the serum phosphate levels are >9 mg/dL, the erdafitinib treatment is interrupted temporarily until serum phosphate levels are <5.5 mg/dL and erdafitinib treatment is re-started at a lower dose.

9. The method of claim 8, wherein the lower dose is 6 mg daily on a continuous basis.

10. The method of claim 1, wherein when the serum phosphate levels are >10 mg/dL, the erdafitinib treatment is discontinued permanently.

11. The method of claim 1, wherein when the serum phosphate levels are >10 mg/dL, the erdafitinib treatment is interrupted temporarily until serum phosphate levels are <5.5 mg/dL and erdafitinib treatment is re-started at a lower dose.

12. The method of claim 1, wherein the at least one FGFR genomic alteration is an FGFR3-TACC3 translocation.

13. The method of claim 1, wherein the at least one FGFR genomic alteration is selected from the following FGFR3 gene mutations: FGFR3 R248C, FGFR3 S249C, FGFR3 G370C, and FGFR3 Y373C.

14. The method of claim 1, wherein the at least one FGFR genomic alteration is selected from the following fusions: FGFR3:TACC3 v1; FGFR3:TACC3 v3; FGFR3:TACC3 Intron; FGFR3:BAIAP2L1; FGFR2:AFF3; FGFR2:BICC1; FGFR2:CASP7; FGFR2:CCDC6, and FGFR2:OFD1.

15. The method of claim 14, wherein the at least one FGFR genomic alteration is an FGFR3-TACC3 fusion.

16. The method of claim 1, wherein the urothelial cancer is metastatic or surgically unresectable urothelial cancer.

17. The method of claim 16, wherein the at least one FGFR genomic alteration is an FGFR3-TACC3 translocation.

18. The method of claim 16, wherein the at least one FGFR genomic alteration is selected from the following FGFR3 gene mutations: FGFR3 R248C, FGFR3 S249C, FGFR3 G370C, and FGFR3 Y373C.

19. The method of claim 16, wherein the at least one FGFR genomic alteration is selected from the following fusions: FGFR3:TACC3 v1; FGFR3:TACC3 v3; FGFR3:TACC3 Intron; FGFR3:BAIAP2L1; FGFR2:AFF3; FGFR2:BICC1; FGFR2:CASP7; FGFR2:CCDC6, and FGFR2:OFD1.

20. The method of claim 1, wherein the amount of 8 mg of erdafitinib is administered as two formulations.

21. The method of claim 20, wherein the two formulations are two tablets, each comprising 4 mg of erdafitinib.

22. The method of claim 1, wherein the amount of 9 mg of erdafitinib is administered as three formulations.

23. The method of claim 22, wherein the three formulations are three tablets, each comprising 3 mg of erdafitinib.

* * * * *

UNITED STATES PATENT AND TRADEMARK OFFICE
CERTIFICATE OF CORRECTION

PATENT NO. : 11,077,106 B2
APPLICATION NO. : 16/483579
DATED : August 3, 2021
INVENTOR(S) : Stuyckens et al.

It is certified that error appears in the above-identified patent and that said Letters Patent is hereby corrected as shown below:

On the Title Page

Item (72) Inventors:
Add inventor – Anne O'Hagan, Lansdale, PA (US)

Signed and Sealed this
Tenth Day of January, 2023

Katherine Kelly Vidal
Director of the United States Patent and Trademark Office